Figure 1:
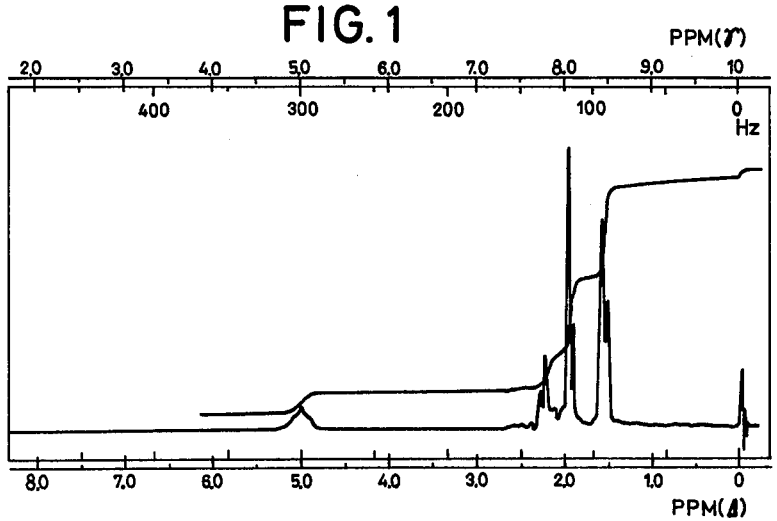

United States Patent [19]

Fujita et al.

[11] 4,105,700
[45] Aug. 8, 1978

[54] PROCESS FOR PREPARING STEREOSPECIFIC NEROLIDOL AND ESTER THEREOF

[75] Inventors: Yoshiji Fujita, Kurashiki; Yoshiaki Omura, Okayama; Takashi Nishida; Kazuo Itoi, both of Kurashiki, all of Japan

[73] Assignee: Kuraray Company, Ltd., Tokyo, Japan

[21] Appl. No.: 778,730

[22] Filed: Mar. 17, 1977

Related U.S. Application Data

[63] Continuation-in-part of Ser. No. 605,455, Aug. 18, 1975, Pat. No. 4,028,385.

[30] Foreign Application Priority Data

| Mar. 12, 1976 | [JP] | Japan | 51-100631 |
| Mar. 12, 1976 | [JP] | Japan | 51-100632 |
| Mar. 23, 1976 | [JP] | Japan | 51-100633 |
| Mar. 12, 1976 | [JP] | Japan | 51-100634 |
| Mar. 19, 1976 | [JP] | Japan | 51-100635 |
| Mar. 19, 1976 | [JP] | Japan | 51-104062 |
| Apr. 26, 1976 | [JP] | Japan | 51-119797 |
| Apr. 26, 1976 | [JP] | Japan | 51-119798 |

[51] Int. Cl.$^2$ .............................................. C07C 29/24
[52] U.S. Cl. ................................................... 568/875

[58] Field of Search .................. 260/631.5; 203/62, 63

[56] References Cited

U.S. PATENT DOCUMENTS

| 1,644,546 | 10/1927 | Ruzicka | 260/631.5 |
| 1,999,110 | 4/1935 | Ruzicka | 260/631.5 |
| 2,848,502 | 8/1958 | Surmatis | 260/631.5 |
| 3,296,080 | 1/1967 | Meuly et al. | 260/631.5 |
| 3,755,469 | 8/1973 | Pasedach et al. | 260/631.5 |

OTHER PUBLICATIONS

Bates, J. Org. Chem., vol. 28, pp. 1086–1089 (1963).
Eliel, Stereochemistry of Carbonyl Compounds, pp. 326–346 (1962).

*Primary Examiner*—Robert Gerstl
*Assistant Examiner*—James H. Reamer
*Attorney, Agent, or Firm*—Flynn & Frishauf

[57] ABSTRACT

A process for obtaining a stereospecific nerolidol at the $\Delta^6$-position thereof by rectifying a mixture of $\Delta^6$-cis-nerolidol and $\Delta^6$-trans-nerolidol in rectification column having from 10 to 100 theoretical plates with a reflux ratio of from 2 to 200 at a temperature below 230° C. under reduced pressure to separate each stereospecific nerolidol from said mixture.

20 Claims, 21 Drawing Figures

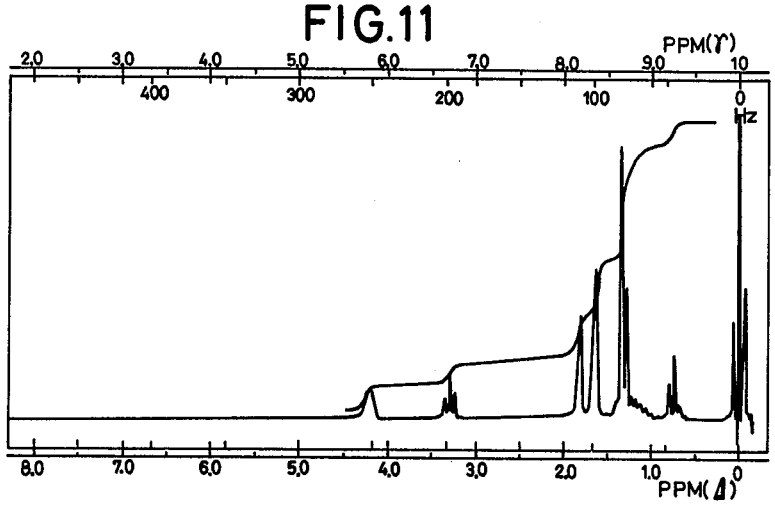
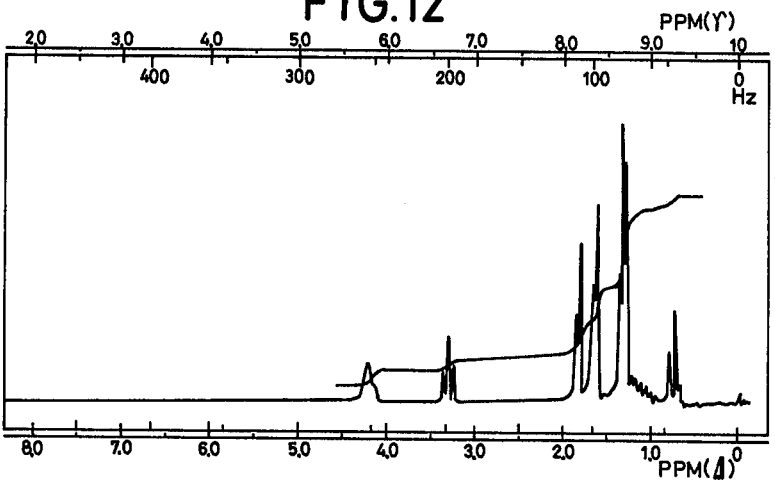

PROCESS FOR PREPARING STEREOSPECIFIC NEROLIDOL AND ESTER THEREOF

RELATED APPLICATION

This application is a continuation-in-part of application Ser. No. 605,455, filed Aug. 18, 1975, now U.S. Pat. No. 4,028,385.

This invention relates to a process for preparing a stereospecific farnesylacetic acid and its esters. Particularly, this invention relates to a process for preparing, respectively, $\Delta^4$-cis-$\Delta^8$-trans-, $\Delta^{4,8}$-trans-, $\Delta^4$-trans-$\Delta^8$-cis- and $\Delta^{4,8}$-cis-farnesylacetic acids and esters thereof. More particularly, this invention relates to a process for preparing $\Delta^{4,8}$-trans-farnesylacetic acid and its ester. The above stereospecific farnesylacetic acids and esters thereof are represented by the following formula (1):

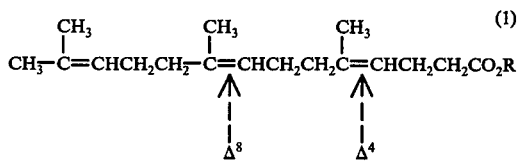

wherein R represents hydrogen atom, an alkyl, alkenyl, alkynyl, cycloalkyl, cycloalkenyl, aryl, aralkyl, aralkenyl or heterocyclic radical having not more than 20 carbon atoms.

Farnesylacetic acid esters are valuable compounds which are employed as medicines having anti-ulcer activity and also as perfumes.

As reported by E. Adami et al in *Med. Exptl.*, 7, 171 (1962) and *J. Med. Chem.*, 6, 457 (1963), the farnesylacetic acid or its esters having the above formula (1) in case where R represents an ethyl group, allyl group, propargyl group, cyclohexyl group, geranyl group or farnesyl group can show anti-ulcer activity, but those wherein R represents a methyl group, propyl group, butyl group, isoamyl group or lauryl group do not show any anti-ulcer activity, while their activities may vary depending upon stereostructure of the double bonds at the $\Delta^4$-position and the $\Delta^8$-position therein.

The farnesylacetic acid and esters thereof having the above formula (1) have four stereoisomers, respectively. More specifically, they involve $\Delta^{4,8}$-cis-form, $\Delta^4$-trans-$\Delta^8$-cis-form, $\Delta^4$-cis-$\Delta^8$-trans-form and $\Delta^{4,8}$-trans-form.

In practice, these isomers have different physical and physiological properties and, when used as a medicine, their respective single forms are preferable. Such single forms are frequently required for the purpose of identification of a substance and of a chemical reagent.

For obtaining these isomers in pure single forms, there may be mentioned either of a stereospecific synthesis method or a separation method of a resultant mixture. The former has drawbacks of considerably complicated procedures and expensive reagents to be applied and, accordingly, this method has been at present regarded as industrially unavailable. Under these circumstances, the latter are being studied in the art.

For separation of these isomers, there has been proposed solely a separation method of farnesylacetic acid geraniol ester as reported by G. Pala et al in *Helv. Chim. Acta.*, 53, 1827 (1970). It is not feasible to separate farnesylacetic acid geraniol ester by distillation or gas chromatography, and a column chromatography technique with silver nitrate should be applied. Such methods are suitable for separation of a small amount of a test sample, but not for industrial treatment of a large amount of a mixture. Then, as a result of our extensive studies in order to find an industrially applicable separation method, we have completed the present invention.

In general, separation of cis-form and trans-form by means of distillation is suitable for separating a mixture of nerol and geraniol as reported by R. B. Bates et al in *J. Org. Chem.*, 28, 1086 (1963), but this separation method has been considered inefficient for its application to such high molecular compounds as farnesol et al. Therefore, it is natural to consider that this separation method is much more difficult for its application to such compounds of high boiling point as the above compounds of formula (1).

However, we have unexpectedly found that the above compounds (1), only where R is a hydrogen atom, a lower alkyl group, a cycloalkyl group, a lower alkenyl group or a cycloalkenyl group, can be relatively easily separated into their respective isomers by means of a rectification, on condition that the compounds comprise not a mixture of the above-mentioned four isomers but a mixture of $\Delta^{4,8}$-cis-form and $\Delta^4$-trans-$\Delta^8$-cis-form or of $\Delta^4$-cis-$\Delta^8$-trans-form and $\Delta^{4,8}$-trans-form and also that the above mixtures of respective two isomers can be easily synthesized, starting from the cis- and trans-forms of geranylacetone. Upon the above findings, we have completed the present invention.

The cis- and trans-form of geranylacetone which may be employed as a starting material in the process of this invention may be a stereospecifically synthesized one, but it is generally practical to separate the forms from a mixture of the cis- and trans-forms.

For separation of a mixture of cis-geranylacetone and trans-geranylacetone are proposed a semicarbazone-recrystallization method reported by O. Isler et al in *Helv. Chim. Acta.*, 39, 897 (1956), a lower temperature crystallization method reported by O. Isler et al in ibid., 43, 1745 (1960), and so on. However, industrially easy separation can preferably be accomplished by means of the rectification method which we have found.

There have been suggested various methods wherein $\Delta^8$-cis, $\Delta^4$-cis- and trans-farnesylacetic acids and their esters or $\Delta^8$-trans, $\Delta^4$-cis- and trans-farnesylacetic acids and their esters are derived from the so obtained cis- or trans-form of geranylacetone. For instance, there are mentioned the following methods:

(a) Wittig reaction of the geranylacetone with γ-bromobutyric acid ester, (b) condensation of farnesyl bromide with diethyl malonate and subsequent hydrolysis and decarboxylation as reported by G. Pala et al in *Helv. Chim. Acta.*, 53, 1927 (1970), (c) condensation of farnesyl bromide with acetoacetic acid ester, heating in an alcohol in the presence of sodium alkoxide and subsequent deacetylation with barium hydroxide as reported by E. Adami et al in *J. Med. Chem.*, 6, 457 (1963), (d) heating nerolidol and orthoacetic acid ester in the presence of an acidic catalyst, as disclosed in our co-pending Japanese Patent Application No. 79448/1973 (U.S. Ser. No. 487,043, now U.S. Pat. No. 3,928,403). However, the most preferable method for mass production in industrial scale is illustratively shown by the following.

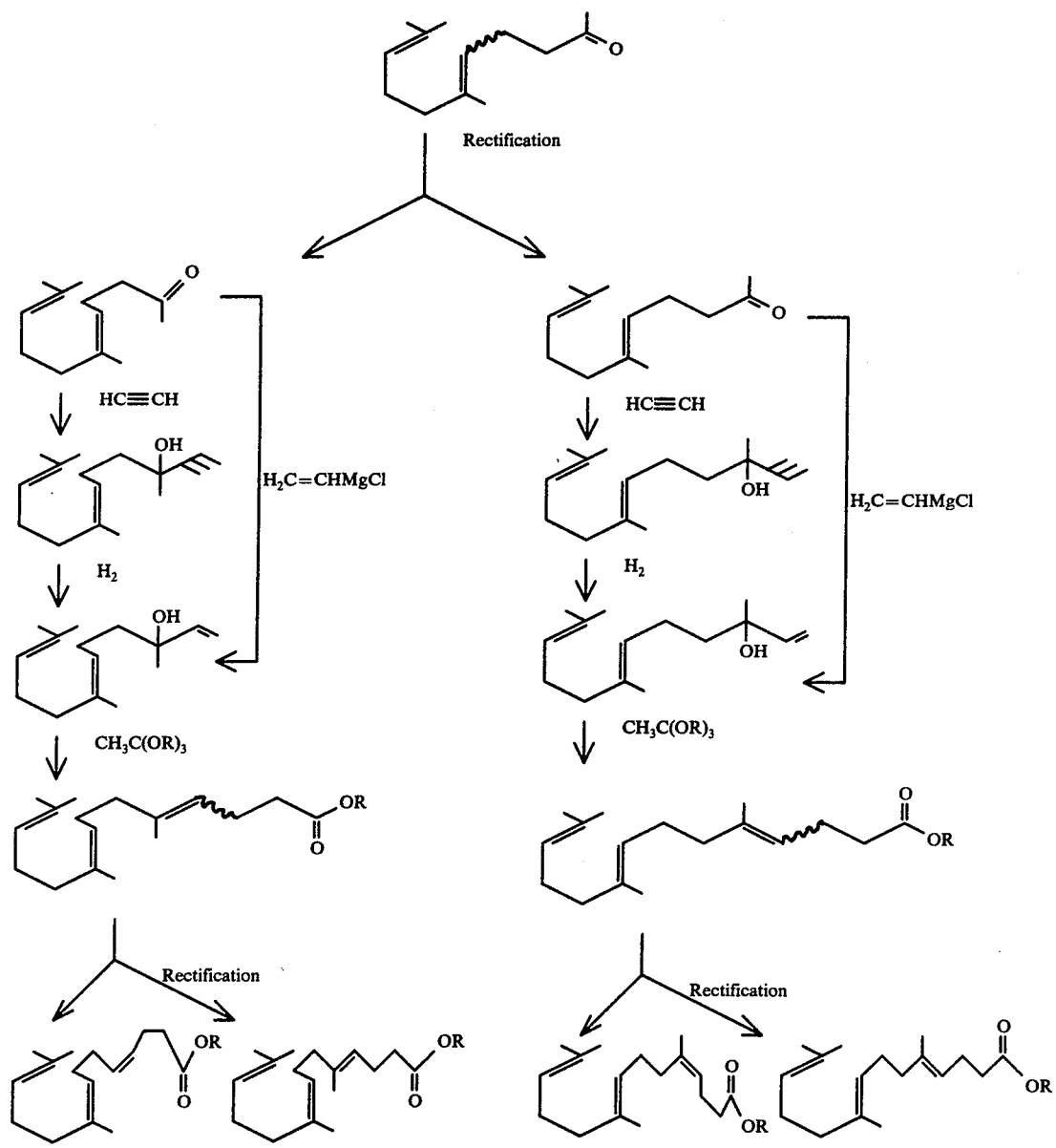

More specifically, the above process is a process wherein a mixture of cis- and trans-geranylacetones is separated by rectification, the geranylacetone is converted to cis- or trans-nerolidol and the so obtained nerolidol is reacted with an orthoacetic acid ester. It is a great advantage of the present process that a small number of steps is involved therein and a total yield thereof is remarkably high.

Next, each step of this invention will be illustrated in detail as follows:

(1) On preparation of Δ⁵-cis- and Δ⁵-trans-geranylacetone Geranylacetone has the following formula:

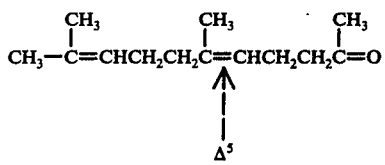

The stereospecific geranylacetone as such is not only used in perfumes, but also very important for preparation of nerolidol and farnesol which are used in perfumes of high grade as well as 3,7,11-trimethyl-2,6,10-dodecatrienoic acid ester having juvenile hormone activity and farnesylacetic acid ester having anti-ulcer activity.

As isolation methods of a mixture of cis- and trans-geranylacetone, there have been known a semicarbon-recrystallization method reported by O. Isler et al in *Helv. Chim. Acta.*, 39, 897–904 (1956) and a recrystallization method at lower temperature reported by O. Isler et al in *Helv. Chim. Acta.*, 43, 1745–1751 (1960), but these methods are impractical in industry because of use of several reagents and complicated operations.

On the other hand, an isolation method by distillation for separation of cis- and trans-isomer, as reported by R. B. Bates et al in *J. Org. Chem.*, 28, 1086–1089 (1963), is suitable for separation of a mixture of nerol and geranylacetone having 10 carbon atoms but supposed to be very ineffective for that of farnesol of higher molecular weight having 15 carbon atoms.

However, we have found that, on rectification of geranylacetone having 13 carbon atoms, the separation of cis- and trans-isomer is very effective and the isomerization cis-isomer ⇄ trans-isomer proceeds catalytically at the same time, and completed this invention.

According to this invention, it is possible to perform the separation of a desired compound in almost quantitative yield in a simple operation without limit to any ratio of cis- and trans-isomer in the starting material.

Also, on preparation of cis-geranylacetone, as the cis-isomer has a lower boiling point that that of the trans-isomer, it is not always necessary to carry it out batchwise, and it can be carried out preferably in a continuous system by taking out the cis-isomer simultaneously with the reaction in the presence of an isomerization catalyst.

As to theoretical plate numbers of a rectifying column for the practice of this invention, it is theoretically possible to separate using a rectifying column having lower theoretical plate numbers, but it is necessary to use at least more than 10 practical plates in the case of obtaining a cis- or a trans-isomer in high purity in a single distillation. Because of the high boiling point of geranylacetone used for separation in this invention, the distillation must be carried out under reduced pressure. For obtaining the desired compound in high yield, the use of a rectifying column having higher number of theoretical plates is preferred, but the use of such a column causes an increase in pressure-loss during distillation. On distillation under reduced pressure, the high pressure-loss causes the stability of distillation to worsen, the temperature of liquid in the still to increase, and the stability of the material to decrease so that the number of plates cannot be increased without limit. From these points of view, as the rectifying column used for this invention, a column having about 10–100 practical plates is preferred and, on consideration of economy, a column having about 20–60 plates is more preferred. As to structure of the column, a column having a small pressure-loss per plate is preferred.

The reflux ratio varies with the structure of the column but is from 2 to 100, preferably about 5–30. The distillation of this invention can be effected in a batchwise, continuous or semibatchwise manner; the manner chosen is determined by ecohomics, including the amount of production.

The isomerization reaction is a reversible reaction and the ratio at equilibrium of cis- and trans-isomers depends on temperature; the ratio is, for example, about 4:6 at 170°–200° C. and about 35:65 at 130°–140° C.

As catalysts used for the isomerization reaction, there can be mentioned transition metal catalysts of the VI, VII or VIII groups such as tungsten, iron, nickel, cobalt, ruthenium, rhenium, platinum, osmium and iridium, and organic sulfur compounds. The tungsten and ruthenium catalysts are practically used in the forms of the following several derivatives: halides, sulfide compounds, chalcogenites, chalcohalides, nitrosochlorides, nitrosylhalides, and salts of inorganic oxonic acids such as sulfates, nitrates, carbonates, arsonates, arsenates, germanium salts, perchlorates, sulfites, nitrites, and salts of aliphatic, alicyclic or aromatic acids or alcohols or phenols, such as acetic acid, propionic acid, oxalic acid, naphthenic acid and sulfonic acid.

As complex catalysts, there can be mentioned chelate compounds of acetylacetonato, benzoylacetonato, glyoximato, quinolato and salicylaldehydato ligands, compounds coordinated with carbon monoxide, monoolefin, diolefin, polyolefin and cyclopentadienyl radicals.

The compounds coordinated with nitrogen compounds, phosphine compounds, arsines, stibines and nitriles may also be used.

Of course, these compounds can be made insoluble by coordinating these compounds with formation of carbon-phosphorus bonding on high molecular compounds such as polyvinylpyridine containing nitrogen and polystyrene compounds so that the recovery process of catalysts can be made easily. These catalysts can be used on active alumina, silica, pumice, fuller's earth and diatomaceous earth.

Among tungsten and ruthenium catalysts, the catalysts having high activities and high selectivities are as follows: tungsten disulfide, complex catalysts such as acetylacetonatoruthenium, glyoximatoruthenium and salicylaldehydatoruthenium and salts such as ruthenium salicylate and ruthenium propionate.

As organic sulfur compounds used for isomerization catalyst, there can be mentioned, for example, phenyldisulfide, alkyldisulfide, phenylmercaptan, thiocresol, alkylmercaptans and thiocarboxylic acid.

The reaction can be performed under air atmosphere but is preferably performed under an inert gas atmosphere in order to elevate the selectivity.

The reaction can be carried out at temperatures of from 50° to 300° C., but preferably at a range of 120°–210° C.

The amount of catalyst used is determined dependent on kinds of catalyst, reaction temperature, economical points and selectivity of the reaction; generally, it is from 0.001 to 20 weight percent of geranylacetone. On reaction at 150°–210° C. using ruthenium and tungsten compounds, it is preferred to be 0.01–10 weight percent, and on reaction at 120°–160° C. using organic sulfur compounds, it is preferred to be 0.1–10 weight percent.

In the case of using organic sulfur compounds as catalysts, it is possible to isomerize radically by adding 0.01–20 percent of radical initiator such as azobisisobutyronitrile (AIBN) and benzoyl peroxide (BPO) to the said organic sulfur compounds, but the isomerization can be well performed with the single use of organic sulfur compounds.

The use of a reaction solvent is not necessary but hydrocarbons such as squalane which are stable and inert to the reaction under the said reaction conditions may be used.

The reaction need not always be continued until the equilibrium composition is obtained and can be stopped on the way. And, in case where the desired compound is a cis-isomer, it is possible to obtain the desired compound in almost quantitative yield by distillation of the mixture under isomerization reaction and by shifting the equilibrium to the formation system.

After the reaction, in case the catalyst is not removed, the reverse-isomerization is apt to occur where the reaction mixture is heated for a long time for rectification so as to separate a trans-isomer at the next step. Therefore, the reaction mixture is subjected to single distillation as separation process of catalyst and, while the distillate is subjected to rectification, the residue containing the catalyst is preferably reused for isomerization reaction. Of course, it is possible to inactivate the catalyst chemically or adsorb it physically or separate it by steam distillation.

(2) On preparation of $\Delta^6$-cis- and $\Delta^6$-trans-nerolidol
Nerolidol has the following formula:

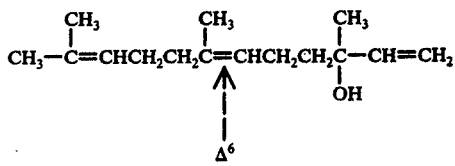

The stereospecific nerolidol as such as a weak but sweet flower odor and is of high grade as a perfume; it is used for preparation of flower essence oils such as jasmine and violet and is very important for preparation of an intermediate of farnesol, 3,7,11-trimethyl-2,6,10-dodecatrienoic acid ester having juvenile hormone activity and farnesylacetic acid ester having anti-ulcer activity.

Nerolidol has been prepared industrially as an intermediate for preparation of isophytol which is used as a starting material for preparation of Vitamin E. Its representative synthetic route is illustrated as follows:

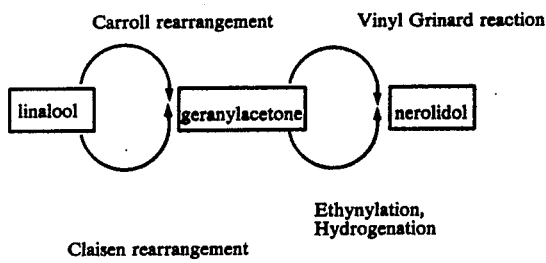

That is, it can be prepared by the following: A process for preparation of nerolidol in high yield which comprises reacting linalool with an equimolar amount of diketene or ethyl acetoacetate, subjecting the resultant to Carroll rearrangement under heating and decarboxylating or subjecting the resultant to Claisen rearrangement by heating it with isopropenyl ether in the presence of an acidic catalyst such as p-toluene-sulfonic acid to obtain geranylacetone and reacting it with a Grignard reagent or ethynylating it and partially hydrogenating the resultant product. But the nerolidol obtained by this method is a mixture of about 4:6 ratio for cis- to trans-isomer.

On the other hand, there has been known a process for preparing stereospecific nerolidol which comprises halogenating $\Delta^2$-cis-3,7-dimethyl-2,6-octadien-1-ol or $\Delta^2$-trans-3,7-dimethyl-2,6-octadien-1-ol as starting materials with, for example, phosphorous tribromide under preservation of stereostructure, condensing the resultant product with ethyl acetoacetate in the presence of an alkali and then hydrolyzing and decarboxylating the resultant product to obtain cis- or trans-geranylacetone and reacting the said compound with vinyl Grignard or ethynylating and partially hydrogenating the said compound. But this process has numerous steps and requires a troublesome procedure for preserving the stereostructure so that it is not suitable for industrial preparation of said compound in large scale. However, we have found a method for separating $\Delta^5$-cis- and $\Delta^5$-trans-geranylacetone, as already described above. The $\Delta^5$-cis- and $\Delta^5$-trans-geranylacetone prepared based on these findings give a stereospecific nerolidol, that is, respectively $\Delta^6$-cis- and $\Delta^6$-trans-nerolidol when they are reacted with a vinyl Grignard reagent or ethylated and partially hydrogenated.

In carrying out the process of this invention, the ethynylation of cis- or trans-geranylacetone can be easily effected in liquid ammonia in the presence of a catalyst, e.g., metallic sodium, metallic potassium, sodium alkoxide, potassium alkoxide, sodium hydroxide, potassium hydroxide et al. The method disclosed in U.S. Pat. No. 3,082,260 may be applied to carry out the ethynylation of the present invention. Partial hydrogenation may be effected, for exayple, by the use of Lindlar catalyst in a lower hydrocarbon, e.g., n-hexane.

Alternative methods according to vinyl Grignard reaction may be conducted by conventional procedures, for example, in such a solvent as tetrahydrofuran or diethyl ether as reported by A. Ofner et al in Helv. Chim. Acta., 42, 2577 (1959). On the other hand, a mixture of cis- and trans-geranylacetone can be used as a starting material for the preparation of a stereospecific nerolidol.

The separation of cis- and trans-isomers by distillation, as reported by R. B. Bates et al in J. Org. Chem., 28, 1086–1089 (1963), is suitable for a mixture of nerol and geraniol having 10 carbon atoms, but it is very ineffective for separation of farnesol having a larger molecular weight with 15 carbon atoms.

However, we have found that the better separation of cis- and trans-isomers of nerolidol can be effected unexpectedly as a result of rectification of nerolidol having 15 carbon atoms. And the isomerization reaction of cis-isomer ⇌ trans-isomer proceeds catalytically.

According to the process of this invention, it is possible to prepare the desired cis- or trans-isomer in a simple operation in almost quantitative yield without limit to any ratio of cis- and trans-isomer in the starting material.

Also, on preparation of cis-nerolidol, as the cis-isomer has a lower boiling point than that of the trans-isomer, it is always unnecessary to carry it out batchwise; preferably, it can be carried out in a continuous system by taking out the cis-isomer simultaneously with the reaction in the presence of the isomerization catalyst.

As to the theoretical plate numbers of a rectifying column for the practice of this invention, it is theoretically possible to separate using a rectifying column having lower theoretical plate numbers, but it is necessary to use at least more than 10 practical plates in the case of obtaining a cis- or trans-isomer in high purity in a single distillation. Because of the fact that nerolidol used for separation of this invention has a very high boiling point and is subject to dehydration by heating, the vacuum distillation must be adopted for distillation. For obtaining the desired compound in high yield, the case of a rectifying column having a higher number of theoretical plates is preferred, but the use of such a column causes an increase in pressure-loss during distillation. On distillation under reduced pressure, the high pressure-loss causes the stability of distillation to worsen, the temperature of liquid in the still to increase, and the stability of the material to decrease, so that the number of plates cannot be increased without limit. From these points of view, as a rectifying column used for this invention, a column having from about 10 to 100 practical plates is preferred, and on consideration of economy, a column having 20–60 plates is more preferred. As to structure of the column, a column having a small pressure-loss per plate is preferred.

The reflux ratio varies with the structure of a column, but is from 2 to 200, preferably about 5–30. The distillation of this invention can be effected in a batchwise, continuation or semi-batchwise manner; the manner chosen in determined by economical considerations, including amount of production.

On separation of $\Delta^6$-cis-nerolidol and $\Delta^6$-trans-nerolidol by rectification, control of temperature is a critical factor. When the temperature rises to 230° C. or over 230° C., dehydration and polymerization of nerolidol take place so that it becomes impossible to continue rectification. Therefore, it is necessary to keep on rectifying at a reduced pressure so as to separate respective stereospecific nerolidols at a bottom temperature below 230° C. At the top of the rectification column, pressure is from about 0.1 to about 5, preferably 0.3 to 2, mmHg. The pressure at the bottom of the column is somewhat higher than that at the top due to some pressure loss. The pressure loss varies with the number of plates in the column. However, said reduced pressures are selected such that the rectification is carried out at a temperature below 230° C. at the bottom of the column.

The isomerization reaction is a reversible reaction and the ratio at equilibrium of cis- and trans-isomers depends on temperature and the ratio is, for example, about 4:6 at 170°–200° C. and about 35:65 at 130°–140° C.

The catalysts used for isomerizing nerolidol are the same as those used for isomerizing geranylacetone, as already described above. The reaction conditions of this isomerization are the same as those for isomerization of geranylacetone.

(3) On preparation of a stereospecific farnesylacetic acid and its esters

The $\Delta^6$-trans- and $\Delta^6$-cis-nerolidol give, respectively, a mixture of $\Delta^4$-cis-$\Delta^8$-trans- and $\Delta^{4,8}$-trans-farnesylacetic acid esters and a mixture of $\Delta^4$-trans-$\Delta^8$-cis- and $\Delta^{4,8}$-cis-farnesylacetic acid esters when they are reacted with orthoacetic acid or its esters. The above reactions are illustrated below:

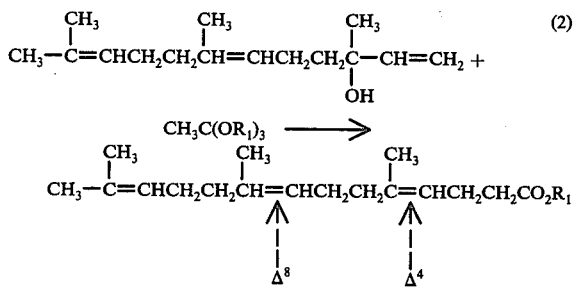

wherein $R_1$ represents a lower alkyl having 1 – 6 carbon atoms, cycloalkyl having 3 – 6 carbon atoms, lower alkenyl having 2 – 6 carbon atoms and cycloalkenyl radical having 3 – 6 carbon atoms.

As lower alkyl radicals having 1 – 6 carbon atoms of $R_1$, there can be mentioned methyl, ethyl, propyl, isopropyl, n-butyl, isobutyl, n-pentyl, isopentyl, n-hexyl and isohexyl radicals et al; as cycloalkyl having 3 – 6 carbon atoms, cyclobutyl, cyclopentyl, and cyclohexyl; as lower alkenyl radicals having 2 – 6 carbon atoms, vinyl, propenyl, butenyl, pentenyl and hexenyl radicals in which the double bond may be at any position; and as cycloalkenyl radicals having 3 – 6 carbon atoms, cyclopentenyl and cyclohexenyl.

The above reaction may be effected by heating in the presence of an acidic catalyst such as aliphatic acids, e.g., acetic acid, propionic acid, butyric acid, isobutyric acid, oxalic acid or adipic acid, or a phenol, e.g., phenol, o-, m- or p-cresol, o-, m- or p-nitrophenol or hydroquinone.

Reaction temperature may be practically between 50° and 200° C., preferably between 130° and 180° C.

The orthoacetic acid ester is theoretically employed in an equimolar amount with respect to nerolidol, but an excess amount thereof may be employed for both reagent and solvent. However, it is preferable in view of a recovery step to employ the ester in an amount of from 1 to 4 times the molar amount of nerolidol.

Catalyst concentration may be practically 0.1 – 20 percent by weight of the starting alcohol, but 1 – 10 percent by weight is preferred in view of reaction rate and selectivity. Lower alcohols are formed in situ as by-products with transesterification as the reaction proceeds and they should be withdrawn out of the reaction system. After completion of the reaction, the reaction mixture may be subjected to vacuum distillation with or without preliminary treatment such as extraction or washing with water.

Usually, the present rearrangement can proceed nearly quantitatively with a conversion of nerolidol of not less than 95 percent and a selectivity to farnesylacetic acid ester of not less than 98 percent. This clearly demonstrates advantages of this invention in an extremely high yield and a single step, as compared with the previously known method, for example, that disclosed in Helv. Chim. Acta., 53, 1827 (1970). A proportion of cis-form to trans-form in the double bond shifted through rearrangement is about 35 : 65.

The compounds obtained by the aforesaid process having the formula (2) are preferable for separation of a mixture of $\Delta^{4,8}$-cis-form and $\Delta^{4,8}$-trans-$\Delta^8$-cis form or of $\Delta^4$-cis-$\Delta^8$-trans-form and $\Delta^{4,8}$-trans-form into each form by rectification. In case of an alkyl or alkenyl group of more than 6 carbon atoms, practical separation is not feasible due to considerably higher boiling point together with lower separation efficiency. More preferable are those compounds wherein an alkyl or alkenyl group has not more than 4 carbon atoms.

Furthermore, we have found that a mixture of farnesylacetic acid esters having 4 isomers gave pure $\Delta^{4,8}$-trans-farnesylacetic acid ester by fractional distillation using a rectifying column with high efficient separation capacity as a result of the extensive investigations with a mixture of farnesylacetic acid esters having the formula (2), wherein $R_1$ represents only the above lower alkyl or lower alkenyl radicals.

Preferred numbers of the theoretical plates installed in a rectifying column employed in the present process of this invention may vary dependent upon kinds of esters used. Ordinarily, it is preferred to use a rectifying column having many plates which can give excellent separation. Although it is possible in principle to separate one of these products even through a rectifying column with a small number of theoretical plates, at least more than 10 practical plates are necessary to obtain the desired $\Delta^{4,8}$-trans-isomer in high purity by one distillatory operation.

The distillation must be carried out under reduced pressure, because the derivatives of farnesylacetic acid have very high boiling points. It is preferable to use a rectifying column with a large number of theoretical plates. But, on the other hand, such a column results in substantial loss of pressure in the column. The number of plates should not be increased without limit, because the increased pressure loss in the column under reduced pressure is disadvantageous in that the stability of distillation is lowered and the product becomes unstable in the still due to the increased temperature.

With respect to the rectifying column employed in this invention, it is preferred to use a column with from 10 to 100 practical plates, more preferably a column with 20 – 60 practical plates, taking economical efficiency into consideration. It is needless to say that a column with a structure which gives little pressure loss per plate is preferable. Reflux ratio is dependent upon the kind of column employed. The distillation is preferably carried out with a reflux ratio of from 2 to 100, more preferably of 5 – 30. By carrying out the distillation with a bottom temperature below 280° C., $\Delta^{4,8}$-trans-isomer is obtained in a particularly high yield. The distillation in this invention can be carried out by batch system, continuous system or semi-batch system. Whether one or the other is the best varies dependent upon economic factors such as output, etc. For example 533 g. of a mixture of ethyl farnesylacetate isomers, which was composed of 15 percent of $\Delta^{4,8}$-cis-isomer, 24 percent of $\Delta^4$-trans-$\Delta^8$-cis-isomer, 23 percent of $\Delta^4$-cis-$\Delta^8$-trans-isomer and 38 percent of $\Delta^{4,8}$-trans-isomer, were fractionated through a rectifying column with 40 theoretical plates with a bottom temperature of 175° C. and a reflux ratio of 10 – 20 to give 150.0 g. of $\Delta^{4,8}$-trans-isomer. The isomer was recovered in a high yield of 74 percent from $\Delta^{4,8}$-trans-isomer in the starting mixture. The separation of $\Delta^{4,8}$-cis-isomer was possible. But, with respect to $\Delta^4$-cis-$\Delta^8$-trans-isomer and $\Delta^4$-trans-$\Delta^8$-cis-isomer, it was almost impossible to separate them respectively in pure form.

In carrying out the separation of the stereoisomers of farnesylacetic acid or its esters by rectification, it is preferred that R in the formula (1) is a hydrogen atom or such a radical as an alkyl, cycloalkyl, alkenyl or cycloalkenyl radical having not more than 6 carbon atoms. In case where R is such a radical as an alkyl or alkenyl having more than 6 carbon atoms, the separation by distillation is difficult in practice, because the efficiency is decreased as the boiling point of the compound is increased. It is preferable that R is such a radical as alkyl or alkenyl having not more than 4 carbon atoms. There may be employed many preparative methods (a)~(d) to synthesize the starting material mixture of $\Delta^4$-cis,trans- and $\Delta^8$-trans,cis-isomers of farnesylacetic acid esters, which are already described above. In manufacturing a large amount of the product industrially, method (d) is the most preferable one. When nerolidol is heated to 100° – 200° C. with orthoacetate in the presence of an acidic catalyst, the alcohol is liberated as the transesterification and Claisen-rearrangement are effected. By removing the alcohol from the reaction system, the desired product is obtained in high yield of more than 95 percent of the conversion based on the amount of nerolidol and more than 98 percent of selectivity to farnesylacetate. The reaction mixture is directly distilled to give farnesylacetate in more than 90 percent based on the starting nerolidol. By further fractionating the distillate mentioned above, $\Delta^{4,8}$-trans-farnesylacetate is separated selectively. When necessary, it may be subjected further to transesterification.

The above rectification can be effected under isomerization.

The isomerization in this invention means a reaction which changes only the configuration at a double bond from cis-form to trans-form and vice versa with no migration of a double bond. Many of the isomerization procedures have been investigated. They are to be classified roughly into three groups:

(A) A method in which isomerization is carried out by producing a double bond again after chemical treatment of a double bond to be isomerized.

(B) A method in which photochemical reaction is applied.

(C) A method in which a catalyst is employed.

To explain more concretely in regard to method (A), an addition reaction to a double bond to be isomerized, such as epoxidation, halogenation, halohydrination, thioetheration or sulfonation, is carried out and subsequently an elimination reaction is conducted to form a mixture of isomers having cis and trans configuration at a double bond. This procedure, as reported by J. W. Cornforth et al in *J. Chem. Soc.*, 1959, 112-127, and ibid., 1959, 1539-2547, has been applied as a method for stereospecific synthesis of squalane. However, this method is complicated in its procedure and not satisfactory in the yield of desired compound. Method (B), in which photochemical reaction is conducted, can effectively change the ratio of cis- and trans-isomers merely by ultraviolet radiation at a low temperature. In this reaction, of course, its selectivity can be increased by using a photosensitizer or a solvent. However, in order to obtain the isomerized product with high selectivity, the reaction should be carried out in a solution of low concentration, the amount of which is about 1 – 10 percent.

Isomerization with a catalyst, method (C), is the most preferable one to manufacture a large amount of product industrially. A catalyst with high selectivity is naturally required to obtain such a compound suitable as pharmaceuticals as farnesylacetic acid or its esters which carries many double bonds and functional groups thereon.

The reaction can be carried out in a homogeneous system at from room temperature to 150° C. in the presence of an acidic catalyst such as phosphoric acid, hydrochloric acid, p-toluenesulfonic acid, zinc chloride or boron trifluoride, etc. It can also be carried out at 100° – 200° C. in the presence of a basic catalyst such as alkali metal alcoholate, sodium hydroxide or potassium hydroxide, etc. Both of the vapor-phase and liquid-phase reactions can be applied by using a catalyst such as silica-alumina or chromium oxide. However, these reactions are accompanied by such a side-reaction as migration of a double bond and production of higher-boiling substances. Therefore, these reactions have an effect when considering the said high selectivity. In addition to the catalysts as mentioned above, catalysts composed of tungsten which belong to group VI, catalysts composed of iodoacetates which belong to group VII or catalysts composed of iron, osmium or iridium which belong to group VIII answer to the purpose of this invention.

More concretely speaking, transition metals which belong to group VI, VII or VIII such as tungsten, iron, nickel, cobalt, ruthenium, rhenium, palladium, platinum, osmium and iridium, etc., are appropriately used as catalysts in the form of several kinds of their derivatives. That is, they are employed in the form of halogenated compounds, sulfides, chalcohalides, nitrosochlorides, nitrosylhalides, salts of inorganic oxo-acids such as sulfates, nitrates, phosphates, carbonates, arsonates, arsenates, germanates, perchlorates, sulfates or nitrites, salts of such organic acids as propionic acid, oxalic acid, or naphthenic acid, alcoholates or phenolates. And they are also used in the form of a chelate such as acetylacetonato, benzoylacetonato, glyoximato, quinolato or salicylaldehydato. As a ligand, carbon monoxide, monoolefin, diolefin, polyolefin or cyclopentadiene may be coordinated. Nitrogen compounds, phosphine compounds, arsines, stibines, or nitriles are appropriately coordinated as a ligand. The recovery of the catalysts used can be easily carried out by coordinating these catalysts to a nitrogen-containing high polymer such as polyvinylpyridine or styrene and by forming carbon-phosphorus bonds to insolubilize them. Naturally, these catalysts can be carried on active alumina, silica, pumice, fuller's earth or kieselguhr. Although most of these catalysts were used as catalysts for the isomerization of allylic alcohols or the dimerization of alkynols as disclosed in British Pat. No. 1,256,184; U.S. patent application Ser. No. 571,004; or Japanese patent application No. 61204/74 (and corresponding U.S. Ser. No. 487,043), we have found that these catalysts might be applicable to steric isomerization reaction between cis-form and trans-form of farnesylacetic acids, esters thereof, geranylacetones and nerolidols. It has been clarified that the ruthenium catalyst shows particularly high activity and selectivity. It is capable of being employed industrially, taking its cost and stability into consideration. Almost all the well-known isomerization reactions using a ruthenium catalyst intended for the migration of double bond can be used. Therefore, it has been considered that its application to this invention is difficult. However, according to our investigations, it is possible to change, by selecting the condition of the amount of catalyst and the reaction temperature, only the stereo-chemical structure from cis to trans or from trans to cis with little migration of a double bond. Among the ruthenium compounds, the chelate compounds, such as acetylacetonato, glyoxymato, quinolato or salicylaldehydato chelate, are most suitable to practice of the present invention. For example, 100 g. of ethyl $\Delta^{4,8}$-cis-farnesylacetate added with 0.1 g. of acetylacetonatoruthenium were heated at 200° C. in an inert atmosphere for 2 hours to give a substance in 45 percent of conversion and 99.5 percent of selectivity, which was composed of 55 percent of $\Delta^{4,8}$-cis-isomer, 25 percent of $\Delta^4$-cis-$\Delta^8$-trans-isomer and $\Delta^4$-trans-$\Delta^8$-cis-isomer, and 20 percent of $\Delta^{4,8}$-trans-isomer. The conversion ratio may be increased up to about 84 percent by continuing the reaction.

The reaction is an equilibrium one. Therefore, a thermo-equilibrated composition of 16 : 48 : 36 of the aforesaid ratio is obtained, starting from any one of $\Delta^{4,8}$-cis-isomer, $\Delta^4$-cis-$\Delta^8$-trans-isomer, $\Delta^4$-trans-$\Delta^8$-cis-isomer or $\Delta^{4,8}$-trans-isomer. The ratio of the component produced is of course dependent upon the reaction temperature.

For example, the ratio of $\Delta^{4,8}$-trans-isomer produced is increased up to about 38 percent at 150° C. and it is decreased to 34 percent at 230° C. The optimum conditions of the reaction temperature, the catalyst concentration, the reaction velocity and the amount of catalyst in industrial manufacturing should be selected. Practically, the time of the reaction need not be so long as to equilibrate the reaction. The conversion may be suppressed at about 20 - 30 percent. As for the amount of the catalyst, if explained by exemplifying acetylacetonatoruthenium, within 0.001 - 20 percent by weight of the catalyst based on farnesylacetic acid or its esters is employed, and the reaction temperature is within 50° - 300° C. The reaction may be carried out in an atmosphere of air. Preferably, the reaction is conducted in an inert atmosphere at a temperature of about 150° - 200° C. in the presence of 0.01 - 1.0 percent by weight of catalyst. Although the reaction can be carried out without the use of a solvent, it may also be carried out with the use of a solvent which is stable and inert under the above-mentioned reaction conditions, e.g., a hydrocarbon such as squalane. When such a catalyst as ruthenium catalyst, which is difficult to remove, is not separated off after isomerization reaction, there is the possibility of the reverse isomerization reaction by heating for a long time in such an operation as rectification. It is preferred that the residue, which contains the catalyst, is recycled to carry out isomerization again after simple distillation to remove the catalyst and the distillate is further rectified.

Of course, chemical deactivation and physical adsorption of the catalyst can be carried out to avoid the reverse isomerization reaction. With the use of the catalyst-system, which is composed of organosulfur compounds and radical initiators, the isomerization reaction also proved to progress selectively as well as with the aforementioned ruthenium catalyst. The isomerization reaction, which is conducted at a temperature of about 50° - 200° C. in the presence of about 0.1 ~ 30 mole percent, based on farnesylacetic acid or its esters, of a sulfur compound such a phenyldisulfide, alkyldisulfide, phenylmercaptan, thiophenol, thiocresol and thiocarboxylic acid, and about 0.01 - 20 percent by weight of radical initiator (e.g., azobisisobutyronitrile (AIBN), benzoylperoxide (BPO)), based on the sulfur compound, gives a thermoequilibrated mixture with high selectivity.

This catalyst is superior to the ruthenium catalyst in that the reverse isomerization reaction is avoidable in rectification because the sulfur compound can be removed by distillation.

(4) Hydrolysis and transesterification of the stereo-specific farnesylacetic acid esters To obtain the stereospecific farnesylacetic acid and its esters having the formula (1) from the stereospecific farnesylacetic acid esters having the formula (2), various methods such as the methods described in U.S. Pat. No. 3,154,570 may be used. Particularly among these methods, hydrolysis and/or esterification or transesterification may be used. As already described above, the separation of farnesylacetic acid esters having more than 6 carbon atoms by rectification is difficult in practice. In cases where R is a radical having larger numbers of carbon atoms, e.g., a geranyl or farnesyl radical, etc., the compound shows an excellent anti-ulcer activity as reported by E. Adami et al in *Med. Exptl.*, 7, 171–176 (1962). As reported by G. Pala et al, however, it is practically impossible to separate their isomers by distillation. In the preparation of these compounds, the most preferable method is to hydrolyze and/or esterify or transesterify the above fractionated compound having the formula (2) to obtain the compound having the formula (1). In the formula (1), R represents hydrogen atom, an alkyl, alkenyl, alkynyl, cycloalkyl, cycloalkenyl, aryl, aralkyl, aralkenyl or heterocyclic radical having not more than 20 carbon atoms. For example, ethyl; allyl; geranyl; farnesyl; cyclobutyl, cyclopentyl; cyclohexyl; cyclopentenyl; cyclohexenyl; propargyl; phenyl or naphthyl which may be substituted with lower alkyl having 1 - 4 carbon atoms, halogen atoms, alkoxy radical having 1 – 4 carbon atoms or nitro radical; furfuryl; phytyl; carvacryl; or cinnanyl radical.

The above hydrolysis and/or esterification or transesterification can be performed by a usual method in the art. Particularly, it is suitable to apply the methods disclosed in the specification of U.S. Pat. No. 3,154,570 at column 2, line 30 to column 3, line 56, or Japanese Patent Publication No. 31088/73 (48-31088), to the exchange of an alcoholic residue $R_1$ of the formula (2) to an alcoholic residue R of the formula (1).

The farnesylacetic acid obtained by the hydrolysis of a mixture of the isomers or by other methods can also be subjected to rectification to give the stereospecific farnesylacetic acid. But this rectification is not so well performed as rectification of the farnesylacetic acid esters having the formula (2) because of its high boiling point and instability to heating.

This invention is illustrated in detail by the following examples, but these are not meant to limit the scope of the invention.

EXAMPLE 1

After 6,016 g. (purity: 95 percent) of linalool and 3,444 g. of diketene were reacted in the presence of 163 g. of triethylamine, 240 g. of aluminum isopropoxide were added and the mixture was subjected to Carroll rearrangement by heating. Vacuum distillation of the reaction mixture gave 5,200 g. of a mixture of cis- and trans-geranylacetone in a ratio of 4 : 6 having b.p. 68° – 74° C. (0.4 mmHg).

Figure 2:
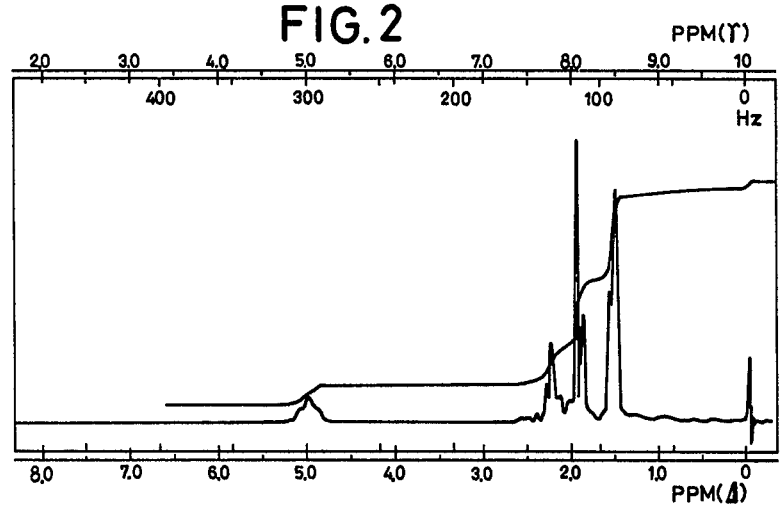

This material was subjected to rectification using a rectifying column having about 40 theoretical plates in a reflux ratio of 10 ~ 20 to give 830 g. of cis-geranylacetone having b.p. 74° – 76° C. (0.4 mmHg) (distillation yield: 40 percent of the cis-isomer charged) and 2,420 g. of trans-geranylacetone having b.p. 77° – 79° C. (0.4 mmHg) (distillation yield: 78 percent of the trans-isomer charged) and 1,950 g. of other intermediate distillate. The refractive index of the said cis-geranylacetone showed $n_D^{30}$ = 1.4628 and its NMR spectrum in carbon tetrachloride is shown in FIG. 1. The refractive index of the said trans-geranylacetone showed $n_D^{30}$ = 1.4634 and its NMR spectrum in carbon tetrachloride is shown in FIG. 2.

Next, 830 g. of the cis-isomer obtained as forerunning and 1,950 g. of the intermediate distillate were mixed and reacted at 140° C. for 8 hours in the presence of 140 g. of p-thiocresol in an atmosphere of nitrogen. The analysis of the reaction mixture by gas chromatography showed that the ratio of cis- and trans-isomer was about 45 : 55. Further rectification of the reaction mixture using a rectifying column having about 40 theoretical plates gave 1,844 g. as forerunning containing p-thiocresol of catalyst and the cis-isomer as main components and 1,070 g. of trans-isomer.

Further, after 1,844 g. of the forerunning was reacted at 140° C. for 12 hours in an atmosphere of nitrogen, the gas chromatographic analysis of the reaction mixture showed that the ratio of cis- and trans-isomer was 42 : 58.

EXAMPLE 2

In a flask provided with a rectifying column having about 40 theoretical plates were placed 1,000 g. of a mixture of cis- and trans-geranylacetone in a ratio of about 4 : 6 and 2.0 g. of acetylacetonatoruthenium (III) and the mixture was rectified at 175°–179° C. of the column bottom temperature and at 130° – 135° C. of the top column temperature at a reduced pressure of 5 – 7 mmHg under reflux ratio 10 to give 968 g. of the distillate, the purity of the cis-isomer of which was 99.4 percent as a result of gas chromatography.

EXAMPLES 3 – 9

A mixture of cis- and trans-geranylacetone in a ratio of 4 : 6 was subjected to rectification in the same manner as in Example 1 and the forerunning obtained in taking out the trans-isomer was isomerized in the presence of several kinds of isomerization catalysts. The reaction mixture was roughly distilled at 120° – 130° C. of the column bottom temperature and the distillate was again rectified to give the trans-isomer. The results were tabulated in Table 1. In Examples 4 and 7, the catalyst was distilled out on rough-distillation, but separated as low-boiling distillate on rectification.

Table 1

| Example | Ratio of cis- - trans-isomer in starting material | catalyst | Condition of isomerization | Ratio of cis-tras-isomer after isomerization | Yield* (%) |
|---|---|---|---|---|---|
| 3 | 72 : 28 | Ru (AA)$_3$ 0.2 wt.% | 180° C  8 hrs. | 46 : 54 | 71 |
| 4 | 67 : 33 | 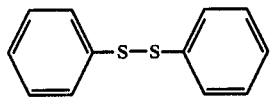 5 wt.% a small amount of BPO | 140° C  18 hrs. | 42 : 58 | 73 |
| 5 | 70 : 30 | 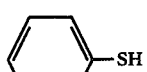 5 wt.% | 140° C  18 hrs. | 42 : 58 | 76 |
| 6 | 70 : 30 | Ru (AA)$_3$ 0.2 wt.% | 190° C  5 hrs. | 47 : 53 | 73 |
| 7 | 70 : 30 | 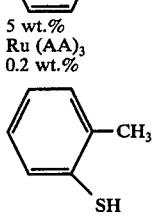 5 wt.% a small amount of AIBN | 140° C  15 hrs. | 42 : 58 | 75 |

Table 1-continued

| Example | Ratio of cis- - trans-isomer in starting material | catalyst | Condition of isomerization | Ratio of cis-tras-isomer after isomerization | Yield* (%) |
|---|---|---|---|---|---|
| 8 | 65 : 35 | RuCl$_2$(PPh$_3$)$_3$ 0.5 wt.% | 170° C 48 hrs. | 50 : 50 | 70 |
| 9 | 65 : 35 | WS$_2$ 0.4 wt.% | 190° C 8 hrs. | 47 : 53 | 64 |

*The yield is that of trans-isomer obtained after separaton of the catalyst and rectification from the reaction mixture after isomerization.

EXAMPLE 10

After 1.5 g. of acetylacetonatoruthenium was added to 500 g. of cis-geranylacetone obtained by Example 2, the mixture was heated at 190° C. in an atmosphere of nitrogen. The reaction mixture was analyzed by gas chromatography. After 2 hours of the reaction, the conversion ratio of cis-isomer was 32 percent and the selectivity of trans-isomer formed 97.4 percent.

After rough-distillation of the product, 472 g. of a mixture of cis- and trans-geranylacetone was obtained, which was subjected to rectification to give 104 g. of cis-isomer, 128 g. of trans-isomer and 240 g. of intermediate distillate.

EXAMPLE 11

1,360 g. of the said mixture of geranylacetone (cis-/trans- $\simeq$ 4/6), which had been obtained in Example 1, was ethynylated in liquid ammonia in the presence of 176 g. of metallic sodium and neutralized with ammonium chloride. The reaction mixture was extracted with ether and the extract was washed with water and dried. After the solvent was distilled off, the residue was subjected to vacuum distillation to afford 1,280 g. of dehydronerolidol having b.p. 110° - 112° C. (0.5 mmHg).

Further, 0.5 ml. of quinoline and 20 g. of 0.25 percent of Pd-Lindlar catalyst was added in a solution of 1,280 g. of the said dehydronerolidol in 2,000 ml. of n-hexane and the mixture was hydrogenated at room temperature and normal pressure. After post-treatment, the reaction mixture was subjected to vacuum distillation to give 1,170 g. of nerolidol having b.p. 105° - 110° C. (0.5 mmHg).

Figure 4:
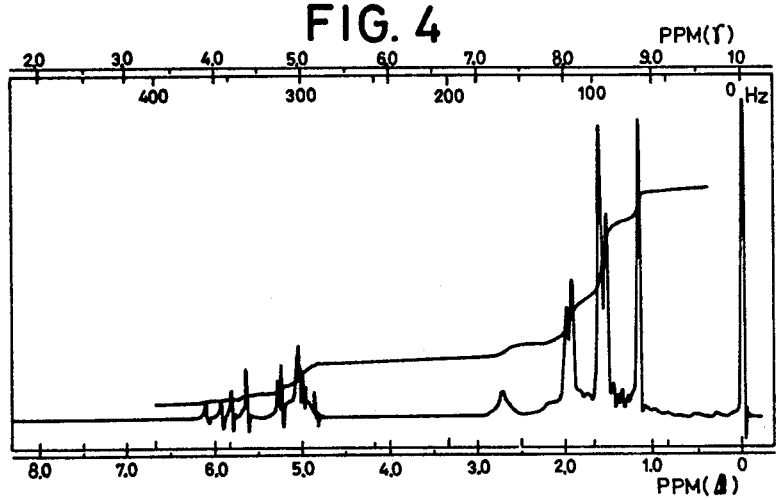
Figure 6:
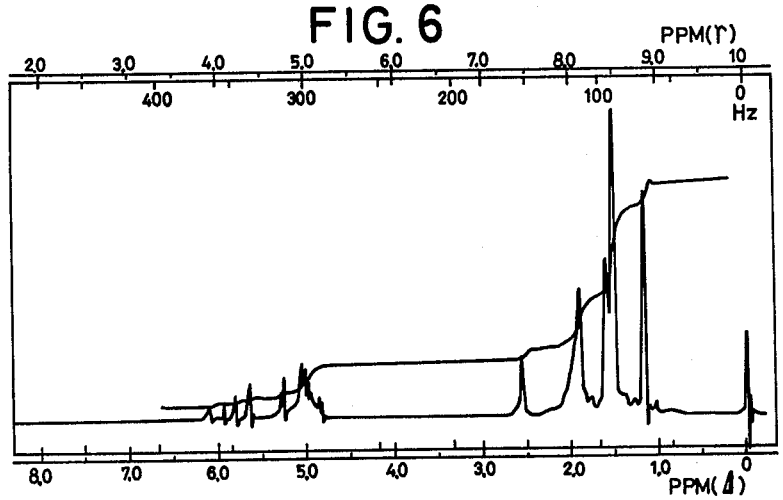

Next, 1,000 g. of a mixture of cis- and trans-nerolidol in a ratio of 40:60 were rectified using a rectifying column having about 40 theoretical plates at 135° - 140° C. of the column bottom temperature at 0.3 - 0.5 mmHg of reduced pressure under reflux ratio of 10 to obtain 183 g. of cis-nerolidol (0.3 mmHg). This yield was 46 percent of distillation yield for cis-isomer charged. Its refractive index was n$_D^{30}$ = 1.4753 and its NMR spectrum in carbon tetrachloride is shown in FIG. 4. 324 g. of trans-nerolidol were obtained from the distillate having b.p. 107° - 110° C. (0.5 mmHg). This was 54 percent of distillation yield for trans-isomer charged. Its refractive index was n$_D^{30}$ = 1.4754 and its NMR spectrum is shown in FIG. 6. 477 g. of intermediate distillate in a ratio of 46:54 of cis- : trans-isomer were also obtained.

Next, 183 g. of cis-isomer obtained as forerunning and 477 g. of the intermediate distillate were mixed to form a mixture of cis- and trans-isomer in a ratio of 61:39. After addition of p-thiocresol, this mixture was isomerized at 140° C. for 4 hours under nitrogen atmosphere. The reaction liquid was analyzed by gas chromatography, which showed that the above ratio was 42:58.

Next, the reaction liquid was roughly distilled at below 130° C. of column bottom temperature to give 632 g. of the distillate. This distillate was rectified as described above using a packed rectifying column having about 40 theoretical plates to give 392 g. of the forerunning in a ratio of 67:33 of cis- : trans-isomer and 227 g. of trans-nerolidol as after-running.

EXAMPLE 12

Figure 3:
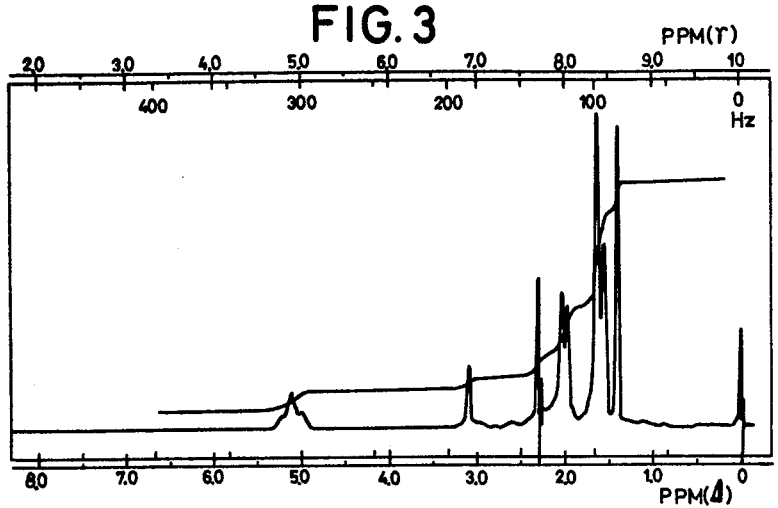

In a 2 liter, three-necked flask, 1 liter of liquid ammonia was placed and, after addition of 55.2 g. of metallic sodium, acetylene gas was passed thereto and continued to pass until the reaction liquid turned from violet to white. 388 g. of cis-geranylacetone was added to the ammonia mixture. While the liquid ammonia was under reflux, acetylene gas was bubbled thereto for 4 hours. After removing the ammonia, 110 g. of ammonium chloride were added and neutralized. The reaction liquid was poured into water and extracted with ether. The extract was washed with water and dried over sodium sulfate and the solvent was distilled off. The residue was subjected to distillation under reduced pressure (0.5 mmHg) in a rectifying column having about 40 theoretical plates (about 30 practical plates) with a reflux ratio of 10 ~ 20 and a bottom temperature of approximately 140° C. to afford 372 g. of cis-dehydronerolidol having b.p. 133° - 135° C. (5 mmHg) in a yield of 85 percent. Its refractive index was n$_D^{30}$ = 1.4750 and its NMR spectrum in carbon tetrachloride is shown in FIG. 3.

Next, in a solution of 320 g. of the said cisdehydronerolidol in 1,000 g. of n-hexane, 0.15 ml. of quinoline and 5.0 g. of 0.25 percent Pd-Lindlar catalyst were added and the mixture was hydrogenated at room temperature under normal pressure. The reaction progress was analyzed with gas chromatography having PEG-20M (5%) at 150° C. of the column temperature. When the cis-dehydronerolidol of the starting material disappeared, the reaction was supposed to be finished and the reaction mixture was filtered out with glass filter. After the filtrate was distilled, the residue was subjected to high vacuum distillation to give 314 g. of cis-nerolidol having b.p. 99° - 102° C. (0.3 mmHg). Its refractive index was n$_D^{30}$ = 1.4753 and its NMR spectrum in carbon tetrachloride is shown in FIG. 4.

Figure 5:
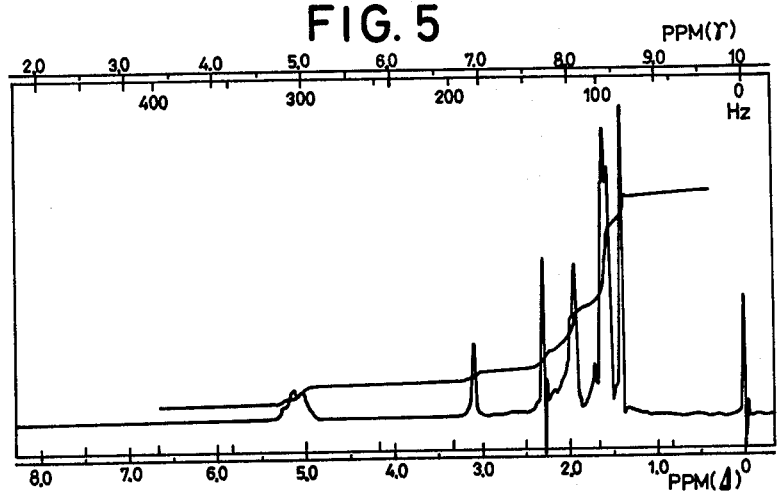

In the same manner, 1,360 g. of trans-geranylacetone was ethynylated in the presence of 176 g. of metallic sodium. After the reaction, 1,280 g. of trans-dehydronerolidol having b.p. 112° C. (0.5 mmHg) was obtained by vacuum distillation in a yield of 83 percent. Its refractive index was n$_D^{30}$ = 1.4771 and its NMR spectrum in carbon tetrachloride is shown in FIG. 5.

Next, in a solution of 1,000 g. of trans-dehydronerolidol 0.5 ml. of quinoline and 15 g. of 0.25 percent Pd-Lindlar catalyst were added and the mixture was hydrogenated at room temperature under normal pressure. After after-treatment, the reaction mixture was subjected to high vacuum distillation to give 980 g. of trans-nerolidol having b.p. 107° - 110° C. (0.5 mmHg). Its refractive index was n$_D^{30}$ = 1.4754 and its NMR spectrum in carbon tetrachloride is shown in FIG. 6.

EXAMPLE 13

According to the method reported by A. Ofner et al in *Helv. Chim. Acta.*, 42, 2577–2584 (1959), cis- or trans-nerolidol was prepared respectively from cis- or trans-geranylacetone. That is, in 420 ml. of tetrahydrofuran were placed 12.5 g. of freshly-prepared metallic magnesium turnings and 60 g. of vinyl bromide were added dropwise thereto under water cooling to form a Grignard reagent. 50 g. cis- or trans-geranylacetone were added dropwise thereto at 25° C. The reaction mixture was neutralized with ammonium chloride and extracted with ether. The extract was dried over sodium sulfate and distilled off under reduced pressure. The residue was subjected to vacuum distillation (1.0 mmHg) in a rectifying column having about 40 theoretical plates (about 30 practical plates) with a reflux ratio of 10 ~ 20 and a bottom temperature of approximately 190° C., to give cis-nerolidol from cis-geranylacetone in a yield of 82 percent. The product was identified by the standard product obtained in Example 12. The trans-isomer was obtained in the same manner.

EXAMPLE 14

In a flask equipped with a rectifying column having about 40 theoretical plates, 500 g. of cis-nerolidol with 30 g. of octadecamercaptan were placed and the mixture was subjected to vacuum distillation at 145° – 150° C. column bottom temperature and 0.7 – 1.0 mmHg of reduced pressure under reflux ratio of 15 to give 482 g. of the distillate, which was analyzed by gas chromatography. The result showed that the ratio of cis- : trans-isomer was 98.4:1.6.

EXAMPLES 15 – 21

A mixture of cis- and trans-nerolidol in a ratio of 4:6 was subjected to rectification in the same manner as in Example 1, and the forerunning which was obtained on taking out trans-isomer was isomerized in the presence of several kinds of isomerization catalysts. After the reaction liquid was roughly distilled at 130° C. of column bottom temperature, the distillate was again subjected to rectification in a rectifying column having about 40 theoretical plates (about 30 practical plates) with a reflux ratio of 10 ~ 20, a bottom temperature of about 190° C. and 1.0 mmHg pressure, to give the trans-isomer. The results are shown in Table 2. In Examples 16 and 19, the catalyst was distilled on rough-distillation, but it was separated as lower boiling part on further rectification.

Table 2

| Example | Ratio of cis-:trans-isomer in starting material | Catalyst | Conditions of isomerization | Ratio of cis-:trans-isomer after isomerization | Yield* (%) |
|---|---|---|---|---|---|
| 15 | 68 : 32 | Ru(AA)₃ 0.4 wt.% | 160° C 6 hrs. | 44 : 56 | 64 |
| 16 | 68 : 32 | 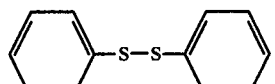 5 wt.% a small amount of BPO | 140° C 7 hrs. | 47 : 53 | 59 |
| 17 | 70 : 30 | 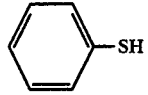 5 wt.% | 140° C 7 hrs. | 42 : 58 | 68 |
| 18 | 70 : 30 | Ru(AA)₃ 0.2 wt.% | 170° C 8 hrs. | 52 : 48 | 43 |
| 19 | 70 : 30 | 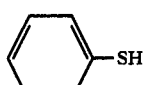 5 wt.% a small amount of AIBN | 140° C 6 hrs. | 43 : 57 | 62 |
| 20 | 65 : 35 | RuCl₂(PPh₃)₃ 0.5 wt.% | 160° C 32 hrs. | 55 : 45 | 41 |
| 21 | 65 : 35 | WS₂ 0.4 wt.% | 180° C 8 hrs. | 49 : 51 | 56 |

*The yield is that of trans-isomer obtained after separation of catalyst and rectification from the reaction mixture after isomerization.

EXAMPLE 22

In a 2 liter, three-necked flask was placed a mixture of 648 g. of ethyl orthoacetate, 440 g. of trans-nerolidol and 22 g. of isobutyric acid and the mixture was heated to 150° – 160° C. The reaction proceeded with a vigorous production of ethanol as a by-product, which was continuously distilled off from the reaction system. The reaction product was analyzed by gas chromatography and disappearance of the starting alcohol indicated completion of the reaction. Isobutyric acid can be added further for more rapid reaction.

The reaction proceeded with a conversion of trans-nerolidol of not less than 95 percent and a selectivity to a mixture of $\Delta^4$-cis-$\Delta^8$-trans- and $\Delta^{4,8}$-trans-farnesylacetic acid ethyl esters of not less than 98 percent. After completion of the reaction, the reaction mixture as such was subjected to vacuum distillation without any after-treatment to afford 533 g. of the desired product in a pure state from distillates of b.p. 148° – 152° C. (0.4 mmHg). This product contained the cis- and trans-formed with respect to its $\Delta^4$-moiety in a proportion of 40 to 60.

The product thus obtained was subjected to distillation using a rectifying tower with not less than 40 theoretical plates and a reflux ratio of 10 – 20 to afford 89 g. of ethyl $\Delta^4$-cis-, $\Delta^8$-trans-farnesylacetate from distillates of b.p. 126° – 128° C. (0.1 mmHg).

Its refractive index $n_D^{30} = 1.4708$.

Figure 7:
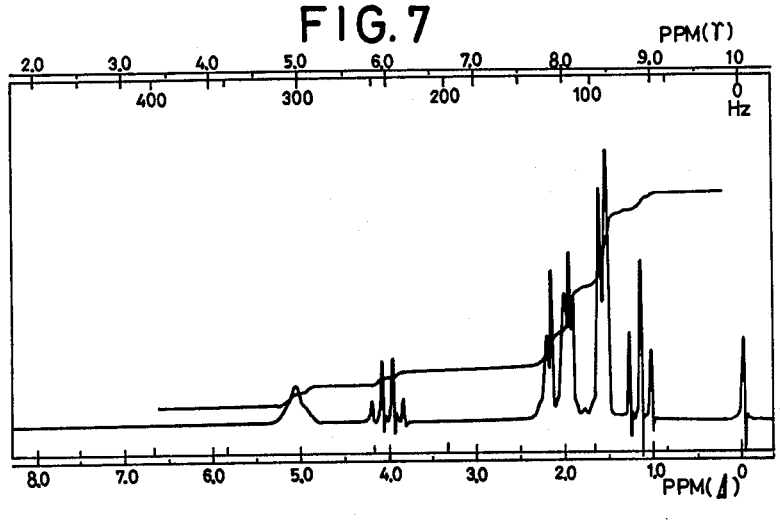

Its nuclear magnetic resonance spectrum in carbon tetrachloride is shown in FIG. 7.

198 g. of ethyl $\Delta^{4,8}$-trans-farnesylacetate were given from distillates of b.p. 130° – 132° C. (0.1 mmHg).

Its refractive index $n_D^{30} = 1.4708$.

Figure 8:
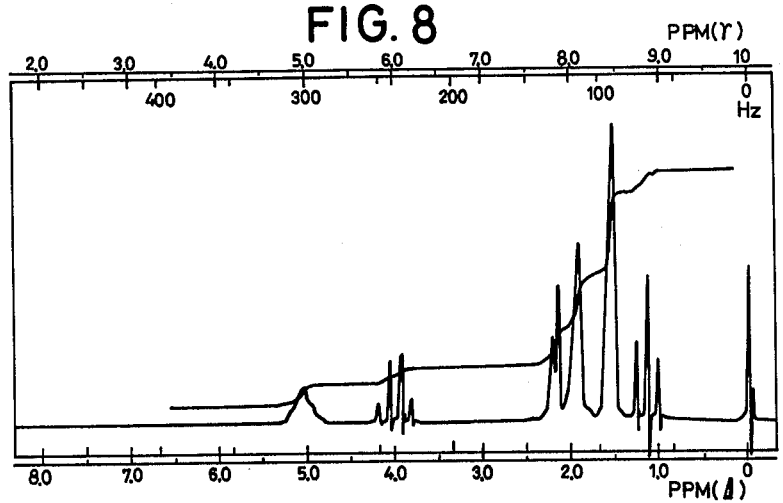

Its nuclear magnetic resonance spectrum in carbon tetrachloride is shown in FIG. 8.

Mass spectra of these products: $[M]^+ = 292$.

EXAMPLE 23

Following the same procedures as in Example 22, the reaction was conducted for 4 hours by heating 424 g. of ethyl orthoacetate, 314 g. of cis-nerolidol and 5.2 g. of isobutyric acid to 150° – 160° C., while the ethanol formed in situ was continuously removed from the reaction system. Isobutyric acid as a catalyst should be supplemented at intervals since the acid was withdrawn from the reaction system. Disappearance of the starting material was confirmed by gas chromatography and vacuum distillation gave 344 g. of a mixture of ethyl $\Delta^{4,8}$-cis- and $\Delta^4$-trans-$\Delta^8$-cis-farnesylacetates from distillates of b.p. 143° – 148° C. (0.4 mmHg). This mixture contained the $\Delta^4$-cis- and $\Delta^4$-trans- forms in a proportion of about 40 to 60. Then, the mixture was distilled by means of a rectifying tower with not less than 40 theoretical plates to give 42 g. of ethyl $\Delta^{4,8}$-cis-farnesylacetate from distillates of b.p. 142° – 144° C. (0.4 mmHg).

Its refractive index: $n_D^{30} = 1.4703$

Figure 9:
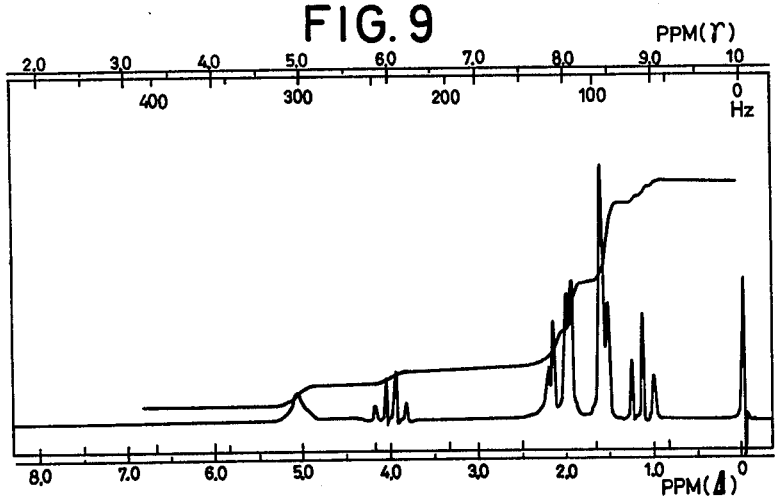

Its nuclear magnetic resonance spectrum in carbon tetrachloride is shown in FIG. 9.

Further, 128 g. of ethyl $\Delta^4$-trans-$\Delta^8$-cis-farnesylacetate was given from distillates of b.p. 146° – 148° C. (0.4 mmHg).

Its refractive index: $n_D^{30} = 1.4708$

Figure 10:
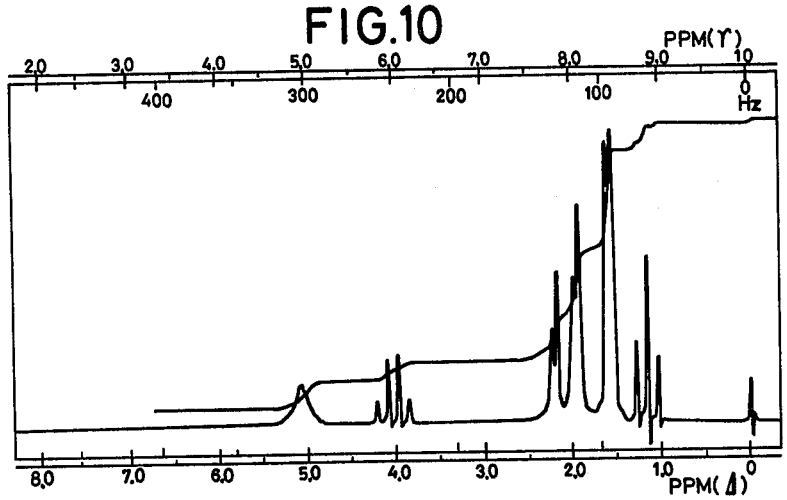

Its nuclear magnetic resonance spectrum in carbon tetrachloride is shown in FIG. 10.

Mass spectra of these compounds: $[M]^+ = 292$.

EXAMPLE 24

Following the same procedure as in Example 22, the reaction was conducted for 6 hours by heating a mixture of 592 g. of n-butyl orthoacetate, 220 g. of cis-nerolidol and 11 g. of hydroquinone to 160° – 165° C., while the n-butanol formed in situ was continuously removed from the reaction system. The reaction mixture as such was subjected to vacuum distillation to give 296 g. of n-butyl $\Delta^{4,8}$-cis- and $\Delta^4$-trans-$\Delta^8$-cis-farnesylacetate. The product was subjected to rectification to give 47 g. of n-butyl $\Delta^{4,8}$-cis-farnesylacetate from distillates of b.p. 133° – 135° C. (0.3 mmHg).

Its refractive index: $n_D^{30} = 1.4695$

Its nuclear magnetic resonance spectrum in carbon tetrachloride is shown in FIG. 11.

Further, 414 g. of n-butyl $\Delta^4$-trans-$\Delta^8$-cis-farnesylacetate was given from distillates of b.p. 135° – 138° C. (0.3 mmHg).

Its refractive index: $n_D^{30} = 1.4698$

Its nuclear magnetic resonance spectrum in carbon tetrachloride is shown in FIG. 12.

EXAMPLE 25

Following the method reported by G. Pala et al in *Helv. Chim. Acta.*, 53, 1827–1832 (1970), a solution of 666 g. of trans-nerolidol, 2,000 ml. of diethyl ether and 20 ml. of pyridine was cooled to −5° C. ∼ −10° C., and a solution of 300 g. of phosphorus tribromide in 500 ml. of diethyl ether was added gradually dropwise thereto at that temperature. After completion of the dropwise addition, the resulting mixture was stirred at that temperature for an additional 12 hours. After completion of the reaction, the reaction mixture was poured into water and neutralized with sodium hydrogen carbonate. The ether layer was washed with water and dried over anhydrous sodium sulfate. The solvent was distilled off at room temperature under reduced pressure to give 760g. of farnesyl bromide with reddish yellow color and irritative odor. This product should be employed as such without any further purification or be kept in a cold place.

Then, a condensation reaction was effected by the use of 501 g. of the so obtained farnesyl bromide and 285 g. of diethyl malonate in 1,500 ml. of ethanol in the presence of 37.1 g. of metallic sodium. The reaction mixture was poured into water and extracted with ether. The ether extract was dried over anhydrous sodium sulfate and the solvent was distilled off. The residue was subjected to vacuum distillation to give 378 g. of diethyl farnesylmalonate from a distillate of b.p. 158° – 160° C. (0.2 mmHg). The ester was then saponified and decarboxylated with 204 g. of potassium hydroxide in 1,000 ml. of ethanol, neutralized with aqueous hydrochloric acid and then extracted with ether. After removing the ether, the residue was subjected to vacuum distillation to give 218 g. of a mixture of $\Delta^8$-trans-$\Delta^4$-cis- and trans-farnesylacetic acids from distillates of b.p. 147° – 150° C. (0.2 mmHg). The product was subjected to fractional distillation by means of a rectifying tower with not less than 40 theoretical plates to give 33 g. of $\Delta^4$-cis-$\Delta^8$-trans-farnesylacetic acid and 87 g. of $\Delta^{4,8}$-trans-farnesylacetic acid from distillates of b.p. 146° – 147° C. (0.2 mmHg) and of b.p. 147° – 149° C. (0.2 mmHg), respectively.

EXAMPLE 26

In a 2 liter, three-necked flask was placed a mixture of 648 g. of ethyl orthoacetate, 440 g. of nerolidol and 22 g. of isobutyric acid, which was then heated at 150° – 160° C. Since the reaction was accompanied by a vigorous side-reaction to produce ethanol, the ethanol was continuously removed from the reaction system. Progress of the reaction was checked by gas chromatography and the reaction should be discontinued at the point of disappearance of the starting nerolidol. In order to accelerate the reaction, a further amount of isobutyric acid can be added. The reaction gave more than 95 percent of the conversion ratio based on the amount of nerolidol and more than 98 percent of the selectivity to ethyl farnesylacetate. The reaction mixture was distilled in vacuo without any post-treatment to give 533 g. of the desired product. b.p. 145° – 152° C. (0.4 mmHg). The result of gas chromatographic analysis showed that this substance was a mixture of stereo-isomers, 15 percent of $\Delta^{4,8}$-cis-isomer, 47 percent of $\Delta^4$-cis-$\Delta^8$-trans- and $\Delta^4$-trans-$\Delta^8$-cis-isomers, and 38 percent of $\Delta^{4,8}$-trans-isomer. Then, the mixture was fractionated through a rectifying column with 40 theoretical plates, which was operated under the conditions of 175° – 185° C. bottom temperature and 10 – 20 reflux ratio, to give 150.0 g. of ethyl $\Delta^{4,8}$-trans-farnesylacetate, b.p. 130° – 132° C. (0.1 mmHg).

Refractive index: $n_D^{30} = 1.4708$

Figure 21:
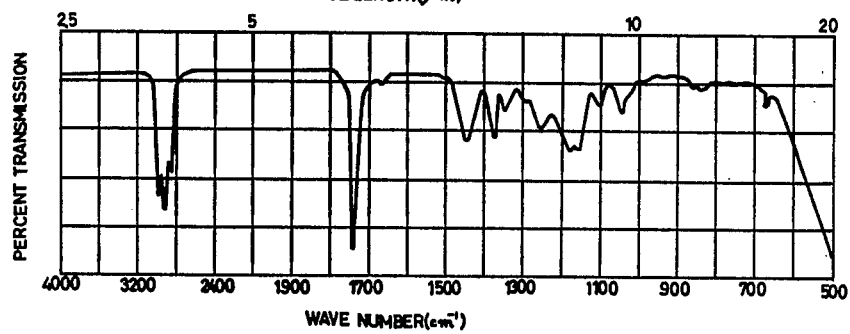

NMR and IR spectra are shown in FIG. 8 and FIG. 21, respectively.

The molecular ion (parent ion) peak [M]+ *was shown at* 292 in mass spectrum.

To 362 g. of ethyl farnesylacetate obtained as the first distillate on rectification, which was composed of 22.1 percent of $\Delta^{4,8}$-cis-isomer, 69.2 percent of $\Delta^4$-cis-$\Delta^8$-trans- and $\Delta^4$-trans-$\Delta^8$-cis isomers, and 8.7 percent of $\Delta^{4,8}$-trans-isomer, were added 11 g. of phenyldisulfide and a small amount of a radical initiator, azobisisobutyronitrile (AIBN for short, hereinafter), and the mixture was heated for 24 hours at 140° C. in a nitrogen atmosphere. After reaction, the above-mentioned ratio was 16.9:50.7:32.4 by gas chromatography. The reaction mixture was roughly distilled in about 0.1 mmHg to give 356 g. of the distillate. Subsequently, this was fractionated through a rectifying column with 40 theoretical plates to give 237.8 g. of the first distillate and 84.2 g. of the second distillate, ethyl $\Delta^{4,8}$-trans-farnesylacetate.

EXAMPLE 27

Following the same procedures as in Example 26, a mixture of 1,184 g. of n-butyl orthoacetate, 220 g. of nerolidol and 22 g. of hydroquinone was reacted with heating at 160° - 165° C. with removal of n-butanol produced from the reaction system. The reaction mixture was directly distilled in vacuo to give 598 g. of n-butyl farnesylacetate, b.p. 134° - 142° C. (0.3 mmHg). Then, this product was fractionated through a rectifying column with 40 theoretical plates and a reflux ratio of 20 to give 147.5 g. of n-butyl $\Delta^{4,8}$-trans-farnesylacetate, b.p. 140° - 142° C. (0.3 mmHg). 64 percent of $\Delta^{4,8}$-trans-isomer introduced was recovered on distillation.

To 437.5 g. of n-butyl farnesylacetate obtained as the first distillate on rectification, which is composed of 21.9 percent of $\Delta^{4,8}$-cis-isomer, 65.6 percent of $\Delta^4$-cis-$\Delta^8$-trans-isomer and $\Delta^4$-trans-$\Delta^8$-cis-isomer, and 12.5 percent of $\Delta^{4,8}$-trans-isomer, 21.8 g. of thiophenol and a small amount of benzoyl peroxide were added. The mixture was heated for 24 hours at 140° C. in a nitrogenous atmosphere. The reaction mixture was analyzed by gas chromatography to show that the above-mentioned ratio of isomers was 16.3:48.8:34.9. The product was directly distilled roughly at a bottom temperature of 150° - 160° C. in 0.1 mmHg to give 418.8 g. of a distillate. Subsequently, the distillate was fractionated through a rectifying column with about 40 theoretical plates to give 308.8 g. of first distillate and 97.4 g. of second distillate, n-butyl farnesylacetates. To 308.8 g. of the above-mentioned first distillate, which is a mixture of 22.1 percent of $\Delta^{4,8}$-cis-isomer, 66.2 percent of $\Delta^4$-cis-$\Delta^8$-trans- and $\Delta^4$-trans-$\Delta^8$-cis-isomers, and 11.7 percent of $\Delta^{4,8}$-transisomer, 15.5 g. of thiophenol and a small amount of benzoyl peroxide were added. The mixture was submitted to isomerization by heating it for 24 hours at 140° C. in a nitrogen atmosphere. Isomers in the reaction mixture were in a ratio of 16.4:49.2:34.4, respectively. The mixture was roughly distilled to give 299 g. of a distillate, which was further fractionated to give 222 g. of first distillate and 66 g. of second distillate, $\Delta^{4,8}$-transisomer.

EXAMPLE 28

Following the procedure reported by G. Pala et al. in *Helv. Chim. Acta.*, 53, 1827–1832 (1970), a mixture of 666 g. of nerolidol (cis:trans = 40:60), 2,000 ml. of diethyl ether and 20 ml. of pyridine was cooled at $-5° \sim -10°$ C. Thereto, 300 g. of phosphorus tribromide were added dropwise slowly at the same temperature. Thereafter, the reaction was completed by further stirring of the mixture for 12 hours at the same temperature. The reaction mixture was poured into water and neutralized with sodium bicarbonate. The ether layer was washed with water and dried over anhydrous sodium sulfate. The solvent was distilled off in vacuo at room temperature to give 760 g. of farnesyl bromide which showed orange color and irritating odor. As this substance was relatively unstable, it was brought to the following reaction without further purification or kept in a cold place.

Then, 501 g. of farnesyl bromide as mentioned above and 285 g. of diethyl malonate in 1,500 ml. of ethanol were subjected to a condensation reaction in the presence of 37.1 g. of metallic sodium. The resulting reaction mixture was poured into water and extracted with ether. The resulting organic layer was dried over anhydrous sodium sulfate. After removing the solvent, the residue was fractionated in vacuo to give 378 g. of diethyl farnesylmalonate, b.p. 155° - 160° C. (0.2 mmHg). This product was saponified and decarboxylated in 1,000 ml. of ethanol with 204 g. of potassium hydroxide. The reaction mixture was neutralized with hydrochloric acid and extracted with ether. After removing the solvent, the residue was fractionated in vacuo to give 218 g. of farnesylacetic acid, b.p. 142° - 150° C. (0.2 mmHg). Gas chromatographic analysis using 5 percent of polyethylene glycol 20 M (PGE-20M, for short) on kieselguhr (60–80 mesh) at 180° C. column temperature, indicated that the substance was a mixture of stereo-isomers, 16 percent of $\Delta^{4,8}$-cis-isomer, 48 percent of $\Delta^4$-cis-$\Delta^8$-trans- and $\Delta^4$-trans-$\Delta^8$-cis-isomers, and 36 percent of $\Delta^4$-trans-$\Delta^8$-trans-isomer. By further fractionation through a rectifying column with 40 theoretical plates, 56.5 g. of $\Delta^{4,8}$-trans-farnesylacetic acid, b.p. 147° - 149° C. (0.2 mmHg) were obtained. This showed that the $\Delta^{4,8}$-trans-isomer was recovered in a yield of 72 percent based on the amount contained in the mixture. Subsequently, 150 g. of farnesylacetic acid, which were obtained as the first distillate, were isomerized by heating with 0.15 g. of acetylacetonatoruthenium $R_U(AA)_3$ at 200° C. in a nitrogenous atmosphere. By gas chromatographic analysis, the ratio of $\Delta^{4,8}$-cis-isomer, ($\Delta^4$-cis-$\Delta^8$-trans-isomer + $\Delta^4$-trans-$\Delta^8$-cis-isomer) and $\Delta^{4,8}$-trans-isomer was 23.3:69.7:7.0 in the starting farnesylacetic acid and was 17.7:52.9:29.4 after isomerization.

The reaction mixture was roughly distilled without further treatment at a bottom temperature of 150° - 160° C. in 0.05 - 0.1 mmHg to give 145.2 g. of a distillate. The abovementioned ratio of the isomers was 18.3:54.7:27.0 by gas chromatographic analysis.

Since the ratio of the isomers was not changed after heating at 200° C. for 4 hours, it was confirmed that the catalyst, $R_U(AA)_3$ was not distilled out of the still. Then, the distillate obtained above was fractionated through a rectifying column with about 40 theoretical plates to give 124 g. of the first distillate and 26.7 g. of the second distillate, $\Delta^{4,8}$-trans-farnesylacetic acid.

EXAMPLES 29 - 31

In Table 3 are shown results of the fractionation of several farnesylacetates, which was carried out at 10 - 20 reflux ratio through a rectifying column with 40 theoretical plates.

EXAMPLES 32 – 38

Following the same procedures as in Example 26, the first distillate, which was obtained when separating the desired $\Delta^{4,8}$-trans-isomer of farnesylacetates, was submitted to isomerization reaction by heating in the presence of several kinds of catalysts. The reaction mixture was roughly distilled at a bottom temperature of 150° – 180° C. and the distillate was further rectified to give $\Delta^{4,8}$-trans-isomer.

Results are shown in Table 4.

Example 22 or 23 was added 0.1 – 10 mole percent of sodium hydroxide or potassium hydroxide and the resulting mixture was heated with 1.5 – 2 molar quantities of geraniol in toluene or xylene to effect a transesterification reaction. After completion of the reaction, the solvent was distilled off and the residue was subjected to high vacuum distillation to give stereospecific farnesylacetic acid geranyl esters in yields of 75 – 85 percent, respectively.

The results are listed in the following Table 5 and they are consistent with those shown by G. Pala et. al.

Table 3

| Example | R in (structure)—OR | Composition* | Recovery** (%) by distillation | Boiling Point*** |
|---|---|---|---|---|
| 29 | $CH_3-$ | 20 : 60 : 20 | 84.2 | 127 – 129° C (0.2 mmHg) |
| 30 | $-CH(CH_3)_2$ | 16 : 48 : 36 | 77.6 | 146 – 148° C (0.2 mmHg) |
| 31 | cyclopentyl | 16 : 48 : 36 | 58.3 | 171 – 173° C (0.2 mmHg) |

*Composition, ($\Delta^{4,8}$-cis-isomer): ($\Delta^4$-trans-$\Delta^8$-cis-isomer + $\Delta^4$-cis-$\Delta^8$-trans-isomer): ($\Delta^{4,8}$-trans-isomer), analyzed by gas chromotography.
**Recovery from $\Delta^{4,8}$-trans-isomer introduced.
***Boiling Point of $\Delta^{4,8}$-trans-isomer.

Table 4

| Example | R—* | Ratio of isomers** before isomerization | Catalyst | Reaction condition | Ratio of** isomers after isomerization | Boiling*** point | Yield**** in per cent |
|---|---|---|---|---|---|---|---|
| 32 | $CH_3-$ | 23.4 : 70.3 : 6.3 | $Ru(AA)_3$ 0.2 wt% | 180° C 8 hrs | 17.5 : 52.3 : 30.2 | 117 – 119° C (0.1 mmHg) | 78.3 |
| 33 | $CH_3-$ | 23.7 : 71.1 : 5.2 | Ph—S—S—Ph 5 wt% a small amount of BPO | 140° C 24 hrs | 16. : 48.1 : 35.8 | " | 84.6 |
| 34 | $C_2H_5-$ | 23.2 : 69.5 : 7.3 | Ph—SH 5 wt% a small amount of AIBN | " | 16.1 : 48.2 : 35.7 | 125 – 127° C (0.1 mmHg) | 74.5 |
| 35 | n-$C_3H_7-$ | 23.1 : 69.1 : 7.8 | $Ru(AA)_3$ 0.2 wt% | 190° C 15 hrs | 17.1 : 51.5 : 31.4 | 136 – 138° C (0.1 mmHg) | 70.7 |
| 36 | n-$C_3H_7-$ | 23.0 : 69.0 : 8.0 | 2-methylthiophenol (CH₃—C₆H₄—SH) 5 wt% a small amount of AIBN | 140° C 24 hrs | 16.3 : 49.0 : 34.7 | " | 71.2 |
| 37 | n-$C_3H_7-$ | 22.9 : 68.7 : 8.4 | $RuCl_2(PPh_3)_3$ 0.5 wt% | 170° C 48 hrs | 18.0 : 54.1 : 27.9 | " | 67.8 |
| 38 | n-$C_4H_9-$ | 24.4 : 65.0 : 10.6 | $WS_2$ 0.4 wt% | 190° C 8 hrs | 18.9 : 56.8 : 24.3 | 131 – 132° C (0.1 mmHg) | 65.9 |

*R in the formula (1).
**Ratio of ($\Delta^{4,8}$-cis-isomer) : ($\Delta^4$-cis-$\Delta^8$-trans-isomer + $\Delta^4$-trans-$\Delta^8$-cis-isomer) : ($\Delta^{4,8}$-trans-isomer).
***The boiling point of $\Delta^{4,8}$-trans-isomers.
****The yield based on $\Delta^{4,8}$-trans-isomer contained in the reaction mixture.

EXAMPLES 39 – 42

To the $\Delta^{4,8}$-cis- or $\Delta^4$-trans-$\Delta^8$-cis- or $\Delta^4$-cis-$\Delta^8$-trans- or $\Delta^{4,8}$-trans-farnesylacetic acid ethyl ester obtained in Example 22 or 23 was added... in *Helv. Chim. Acta.*, 53, 1827 (1970).

Table 5

Figure 13:
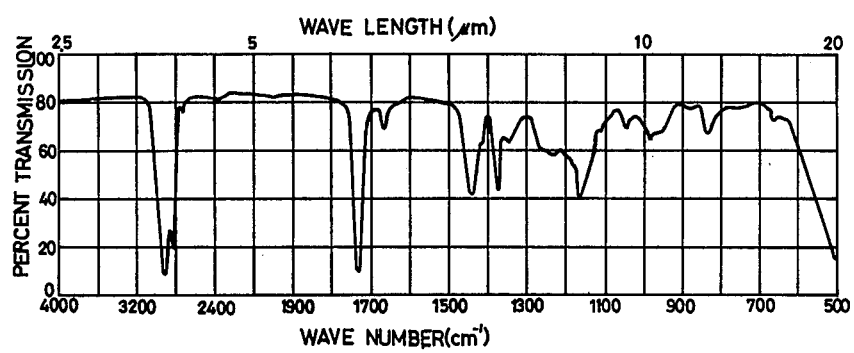
Figure 14:
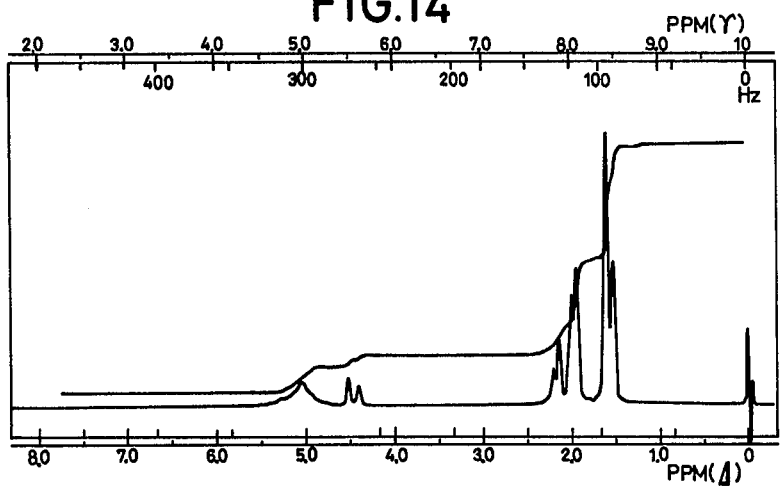
Figure 15:
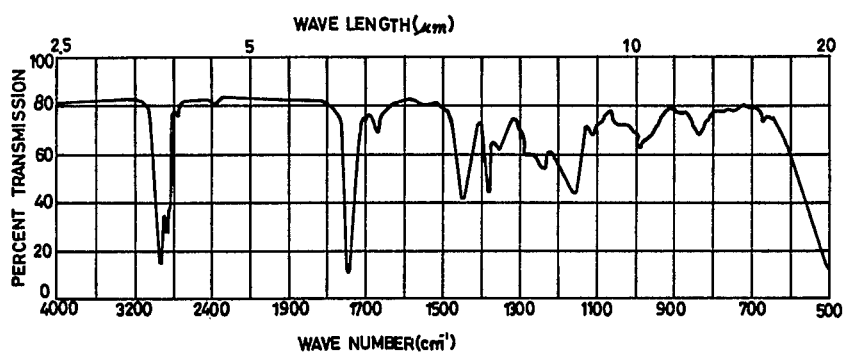
Figure 16:
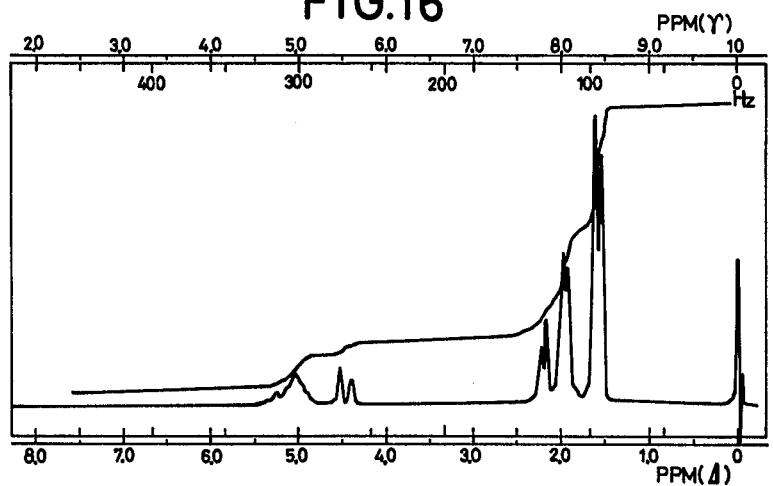
Figure 17:
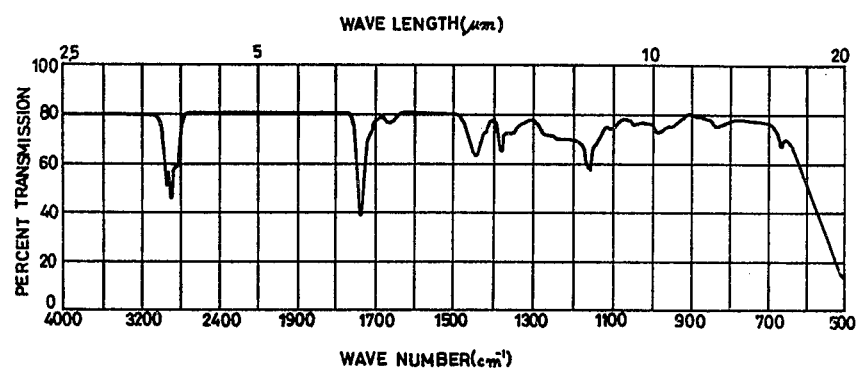
Figure 18:
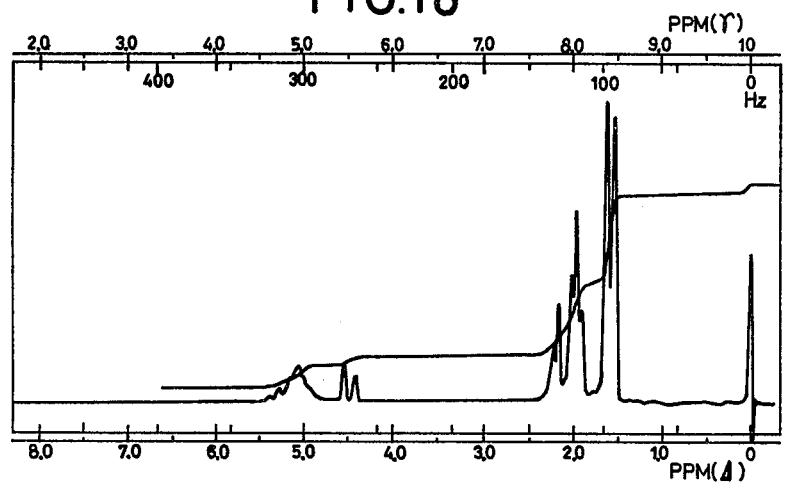

| Example | (structure)—$CO_2Ge$* | b.p. (° C, 0.1 mmHg) | $n_D^{30}$ | IR spectrum | NMR spectrum |
|---|---|---|---|---|---|
| 39 | $^{4,8}$-cis- | 190 – 195 | 1.4870 | FIG. 13 | FIG. 14 |
| 40 | $^4$-trans- $^8$-cis- | 193 – 198 | 1.4872 | FIG. 15 | FIG. 16 |
| 41 | $^4$-cis- $^8$-trans- | 197 – 203 | 1.4869 | FIG. 17 | FIG. 18 |
| 42 | $^{4,8}$-trans- | 201 – 206 | 1.4878 | FIG. 19 | FIG. 20 |

*Ge represents a geranyl radical.

EXAMPLE 43

$\Delta^{4,8}$-trans-farnesylacetic acid, which was obtained in Example 28, and two times the amount thereof of geraniol were refluxed in benzene or toluene for 8 hours in the presence of 0.1 - 0.2 mole percent of p-toluene-sulfonic acid as a catalyst. Water liberated was removed continuously from the reaction system. Then the organic layer was washed three times with an aqueous solution saturated with sodium bicarbonate and dried over anhydrous sodium sulfate. After distilling off the solvent, the residue was fractionated under reduced pressure to give geranyl ester of farnesylacetic acid, b.p. 201° - 206° C. (0.1 mmHg) in 65 - 75 percent yield.

Refractive index of this compound: $n_D^{30} = 1.4878$.

Figure 19:
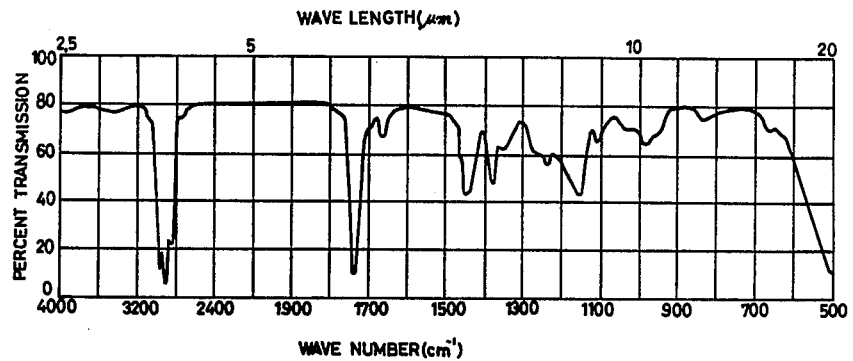
Figure 20:
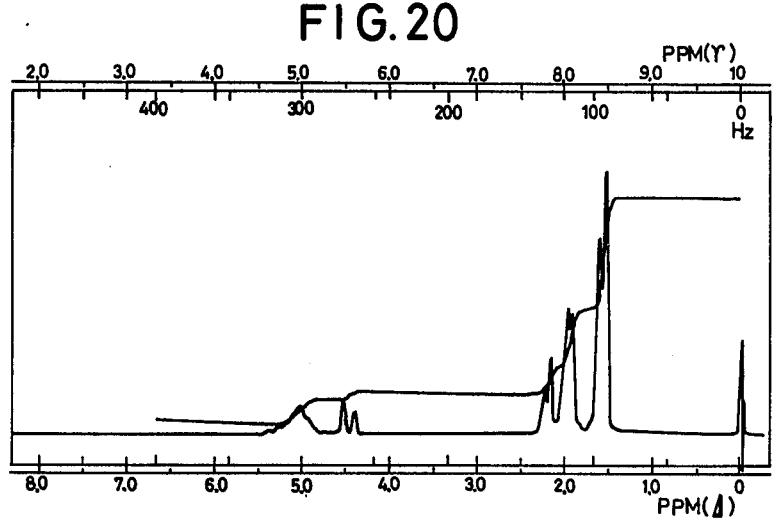

NMR and IR spectra are shown in FIG. 20 and FIG. 19, respectively.

What is claimed is:

1. A process for obtaining a stereospecific nerolidol at the $\Delta^6$ position thereof and having the formula:

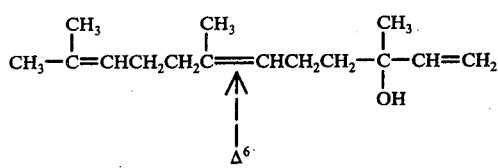

which comprises rectifying a mixture of $\Delta^6$-cis-nerolidol and $\Delta^6$-trans-nerolidol in a rectification column having from 10 to 100 theoretical plates with a reflux ratio of from 2 to 200 at a temperature below 230° C. under reduced pressure of from 0.1 to 5 mm Hg at the top of said column to separate each stereospecific nerolidol from said mixture.

2. The process according to claim 1, wherein one of the components or a mixture containing the same obtained by the rectification is heated in the presence of an isomerization catalyst, and the resulting isomerization reaction mixture is re-rectified to recover the other component of the stereospecific nerolidols.

3. The process for obtaining $\Delta^6$-cis-nerolidol according to claim 1, wherein said rectification of a mixture comprising $\Delta^6$-cis- and $\Delta^6$-trans-nerolidols is conducted in the presence of an isomerization catalyst to isomerize the trans-isomer to the cis-isomer.

4. The process according to claim 1, wherein said rectification is conducted with a rectification column having from 2 to 60 theoretical plates with a reflux ratio of from 5 to 30.

5. The process according to claim 2, wherein said isomerization catalyst is a compound of a transition metal of Group VI, VII or VIII of the Periodic Table, or an organic sulfur compound.

6. The process according to claim 5, wherein said isomerization catalyst is a ruthenium compound.

7. The process according to claim 5, wherein said isomerization catalyst is a tungsten compound.

8. The process according to claim 5, wherein said isomerization catalyst is an organic sulfur compound.

9. A process for preparing a stereospecific nerolidol at the $\Delta^6$-position thereof and having the formula:

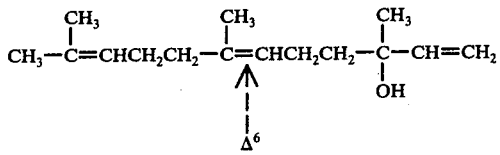

which comprises (1) rectifying a mixture of $\Delta^5$-cis- and $\Delta^5$-trans-geranylacetone having the formula:

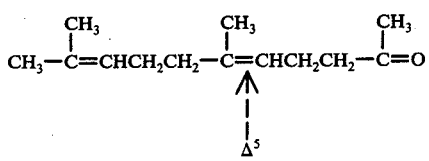

to obtain each isomer thereof, and (2) subjecting said cis- or trans-isomer to vinylation.

10. The process according to claim 9, which comprises heating the residual component obtained by the rectification of a mixture of $\Delta^5$-cis- and $\Delta^5$-trans-geranylacetone, in the presence of an isomerization catalyst to enrich each one of the isomers, re-rectifying the resulting reaction product to recover each stereo-isomeric geranylacetone, and subjecting each stereo-generic geranylacetone to vinylation.

11. The process according to claim 10, wherein said isomerization catalyst is a compound of a transition metal of Group VI, VII or VIII of the Periodic Table, or an organic sulfur compound.

12. The process according to claim 9, wherein said rectification is conducted in a rectification column having from 10 to 100 theoretical plates with a reflux ratio of from 2 to 200 at a temperature below 230° C. under reduced pressure.

13. The process according to claim 11, wherein said rectification is conducted with a rectification column having from 20 to 60 theoretical plates with a reflux ratio of from 5 to 30.

14. The process for preparing $\Delta^6$-cis-nerolidol according to claim 9, which comprises rectifying a mixture of $\Delta^5$-cis- and $\Delta^5$-trans-geranylacetone in the presence of an isomerization catalyst to isomerize the trans-isomer to the cis-isomer.

15. A process for preparing a stereospecific nerolidol at the $\Delta^6$-position thereof and having the formula:

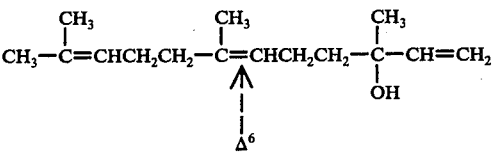

which comprises (1) rectifying a mixture of $\Delta^5$-cis- and $\Delta^5$-trans-geranylacetone having the formula:

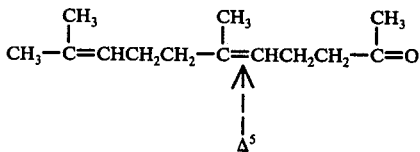

to obtain each isomer thereof, and (2) ethynylating said cis- or trans-isomer and partially hydrogenating the resulting reaction product, $\Delta^6$-cis-nerolidol being so formed from $\Delta^5$-cis-geranylacetone and $\Delta^6$-trans-nerolidol being so formed from $\Delta^5$-trans-geranylacetone.

16. The process according to claim 15, which comprises heating the residual component obtained by rectification of a mixture of $\Delta^5$-cis- and $\Delta^5$-trans-geranylacetone, in the presence of an isomerization catalyst to enrich each one of the isomers, re-rectifying the resulting reaction product to recover each stereo-isomeric geranylacetone, and subjecting each stereo-isomeric geranylacetone to (2).

17. The process according to claim 16, wherein said isomerization catalyst is a compound of a transition metal of Group VI, VII or VIII of the Periodic Table, or an organic sulfur compound.

18. The process according to claim 15, wherein said rectification is conducted in a rectification column having from 10 to 100 theoretical plates with a reflux ratio of from 2 to 200 at a temperature below 230° C. under reduced pressure.

19. The process according to claim 18, wherein said rectification is conducted with a rectification column having from 20 to 60 theoretical plates with a reflux ratio of from 5 to 30.

20. The process for preparing $\Delta^6$-cis-nerolidol according to claim 15, which comprises rectifying a mixture of $\Delta^5$-cis- and $\Delta^5$-trans-geranylacetone in the presence of an isomerization catalyst to isomerize the trans-isomer to the cis-isomer.

* * * * *

UNITED STATES PATENT AND TRADEMARK OFFICE
CERTIFICATE OF CORRECTION

PATENT NO. : 4,105,700
DATED : August 8, 1978
INVENTOR(S) : YOSHIJI FUJITA et al It is certified that error appears in the above-identified patent and that said Letters Patent are hereby corrected as shown below:

Title page, [73] Assignee: should read as follows

--Kuraray Company, Ltd., Okayama-ken, Japan--.

Title Page, [30] Foreign Application Priority Data should read as follows

```
-- Sept.  2, 1974  [JP] Japan........49-100631
   Sept.  2, 1974  [JP] Japan........49-100632
   Sept.  2, 1974  [JP] Japan........49-100633
   Sept.  2, 1974  [JP] Japan........49-100634
   Sept.  2, 1974  [JP] Japan........49-100635
   Sept. 10, 1974  [JP] Japan........49-104062
   Oct.  17, 1974  [JP] Japan........49-119797
   Oct.  17, 1974  [JP] Japan........49-119798 --.
```

Column 8, line 11 - "exayple" should be --example--.

Signed and Sealed this

Thirty-first Day of July 1979

[SEAL]

Attest:

*Attesting Officer*

LUTRELLE F. PARKER
*Acting Commissioner of Patents and Trademarks*